US008778611B2

(12) United States Patent
Chalker et al.

(10) Patent No.: US 8,778,611 B2
(45) Date of Patent: Jul. 15, 2014

(54) *MYCOPLASMA GENITALIUM* DETECTION ASSAY BASED ON THE MG219 GENE

(75) Inventors: Vicki Chalker, London (GB); Cathy Ison, London (GB)

(73) Assignee: The Secretary of State for Health, London (GB)

( * ) Notice: Subject to any disclaimer, the term of this patent is extended or adjusted under 35 U.S.C. 154(b) by 949 days.

(21) Appl. No.: 12/302,752

(22) PCT Filed: May 24, 2007

(86) PCT No.: PCT/GB2007/001913
§ 371 (c)(1),
(2), (4) Date: Dec. 14, 2009

(87) PCT Pub. No.: WO2007/138271
PCT Pub. Date: Dec. 6, 2007

(65) Prior Publication Data
US 2010/0089751 A1    Apr. 15, 2010

(30) Foreign Application Priority Data

May 26, 2006 (GB) .................................. 0610522.5

(51) Int. Cl.
*C12Q 1/68* (2006.01)
*C07H 21/02* (2006.01)
*C07H 21/04* (2006.01)

(52) U.S. Cl.
USPC ......... 435/6.15; 435/6.1; 435/6.11; 435/6.12; 435/91.2; 536/23.7; 536/24.32; 536/24.33

(58) Field of Classification Search
None
See application file for complete search history.

(56) References Cited

U.S. PATENT DOCUMENTS 5,541,308 A * 7/1996 Hogan et al. .................. 536/23.1
6,482,589 B1  11/2002 Weisburg

FOREIGN PATENT DOCUMENTS

WO     98/11259 A3    3/1998
WO     03/040689 A3   5/2003

OTHER PUBLICATIONS

NCBI Database. National Center for Biotechnology Information, National Library of Medicine (Bethesda, MD, USA) GenBank Accession No. L43968, Jan. 9, 2006, nucleotides 265561-266160.*
Mitsuhashi et al al. Journal of Laboratory Analysis. 1996. 10: 285-293.*
NCBI Database, National Center for Biotechnology Information. GenBank Accession No. L43967, Jan. 9, 2006, nucleotides 265561-266160.*

Adams, D.J., et al., Database Accession No. CR213596, "Reverse Strand Read From Insert in 5' HPRT Insertion Targeting and Chromosome Engineering Clone MHPN72b08," Database EMBL [Online], Jul. 6, 2004, <http://www.ebi.ac.uk/ebisearch/search.ebi?db=nucleotidesequences&query=cr213596> [retrieved Apr. 9, 2007], 1 page.
Anderson, O.D., et al., "The Structure and Function of the Expressed Portion of the Wheat Genomes—Meiotic Anther cDNA Library" (unpublished), Database Accession No. CA483934, "Wheat Meiotic Anther cDNA Library Triticum aestivum cDNA Clone WHE3207_B12_D23, mRNA Sequence," Database EMBL [Online], Nov. 15, 2002, <http://www.ebi.ac.uk/ebisearch/search.ebi?db=nucleotidesequences&query=ca483934> [retrieved Mar. 9, 2007], 2 pages.
Dias Neto, E., et al., "Shotgun Sequencing of the Human Transcriptome With ORF Expressed Sequence Tags," Proceedings of the National Academy of Sciences 97(7):3491-3496, 2000.
Dupin, N., et al., "Detection and Quantification of *Mycoplasma genitalium* in Male Patients With Urethritis," Clinical Infectious Diseases: An Official Publication of the Infectious Diseases Society of America 37(4):602-605, Aug. 2003.
Jensen, J.S., et al., "Use of TaqMan 5' Nuclease Real-Time PCR for Quantitative Detection of *Mycoplasma genitalium* DNA in Males With and Without Urethritis Who Were Attendees at a Sexually Transmitted Disease Clinic," Journal of Clinical Microbiology 42(2):683-692, Feb. 2004.
Kohara, Y., et al., "EST Analysis of Gene Expression in Unfertilized Eggs and Gastrula of the Starfish, *Asterina pectinifera*" (unpublished), Database Accession No. DB396383, "*Asterina pectinifera* cDNA Clone:ape33n04, 5' End," Database EMBL [Online], Apr. 1, 2006, <http://www.ebi.ac.uk/ebisearch/search.ebi?db=nucleotidesequences&query=db396383> [retrieved Mar. 9, 2007], 1 page.
McCarter, J.P., et al., "The Washington University Nematode EST Project, 1999" (unpublished), Database Accession No. BF013394, "*Meloidogyne javanica* Egg SL1 Topo2 Kloek Chiapelli McCarter *Meloidogyne javanica* cDNA 5', mRNA Sequence," Database EMBL [Online], Oct. 13, 2000, <http://www.ebi.ac.uk/ebisearch/search.ebi?db =nucleotidesequences&query=bf013394> [retrieved Mar. 9, 2007], 2 pages.
Musatovova, O., et al., "Transcriptional Starts for Cytadherence-Related Operons of *Mycoplasma genitalium*," FEMS Microbiology Letters 229(1)73-81, Dec. 2003.
"National Cancer Institute, Cancer Genome Anatomy Project (CGAP)" (unpublished), Database Accession No. AA917542, "*Homo sapiens* cDNA Clone Image:1535434 3' Similar to TR:Q33563 Q33563 EATRO 164 Kinetoplast, mRNA Sequence," Database EMBL [Online], Apr. 22, 1998, <http://www.ebi.ac.uk/ebisearch/search.ebi?db=nucleotidesequences&query=aa917542> [retrieved Mar. 9, 2007], 1 page.
Smith, T.P.L., et al., "A Second Set of Bovine ESTs From Pooled-Tissue Normalized Libraries" (unpublished), Database Accession No. CB427824, "*Bos taurus* cDNA 3', mRNA Sequence," Database EMBL [Online], Mar. 26, 2003, <http://www.ebi.ac.uk/ebisearch/search.ebi?db=nucleotidesequences&query=cb427824> [retrieved Mar. 9, 2007], 1 page.

(Continued)

*Primary Examiner* — Carla Myers
(74) *Attorney, Agent, or Firm* — Christensen O'Connor Johnson Kindness PLLC

(57) ABSTRACT

There is provided a method for detecting *M. genitalium* nucleic acid in a sample, comprising: (i) amplifying a nucleic acid sequence comprising a fragment of SEQ ID NO: 1 (Mg219 gene); and (ii) detecting said amplified nucleic acid sequence.

156 Claims, 12 Drawing Sheets

(56) References Cited

OTHER PUBLICATIONS

Yoshida, T., et al., "Quantitative Detection of *Mycoplasma genitalium* From First-Pass Urine of Men With Urethritis and Asymptomatic Men by Real-Time PCR," Journal of Clinical Microbiology 40(4):1451-1455, Apr. 2002.

Dutro, S.M., et al., "Development and Performance of a Microwell-Plate-Based Polymerase Chain Reaction Assay for *Mycoplasma genitalium*," Sexually Transmitted Diseases 30(10):756-763, Oct. 2003.

Eastick, K., et al., "A Novel Polymerase Chain Reaction Assay to Detect *Mycoplasma genitalium*," Molecular Pathology 56(1):25-28, Feb. 2003.

Jurstrand, M., et al., "Detection of *Mycoplasma genitalium* in Urogenital Specimens by Real-Time PCR and by Conventional PCR Assay," Journal of Medical Microbiology 54(1):23-29, Jan. 2005.

Razin, S., "DNA Probes and PCR in Diagnosis of *Mycoplasma* Infections," Molecular and Cellular Probes 8(6):497-511, Dec. 1994.

Svenstrup, H.F., et al., "Development of a Quantitative Real-Time PCR Assay for Detection of *Mycoplasma genitalium*," Journal of Clinical Microbiology 43(7):3121-3128, Jul. 2005.

\* cited by examiner

Figure 1

-11 catagttcatt 1 atgcgcacca gttacttgaa aaaaataccc ataatgaata gtgatagtga tctaaaactc
            61 caaaaggtgt ggatcgagcg ggatgttgat caagatgaac ttagtttaac aactactgca
           121 gttgaactta aaaagagtga tgaacaaaaa cctgttgcca ttaaaagtag tgactttatt
           181 ggtcatgaag agttaatctc tgttccagtt ttactaatcc caacccctgt tgttaaagag
           241 attgatcaac cagcagttat tcctccagtt aaagcaaaac caaaagcaac taaaaagaaa
           301 actcctgtta aatcaaaacc aactagtaaa tcaactaaac aaacaaaacc taaacaatcc
           361 aagcccaaat caaaacaagt tcaacaaacc aaagctaaac caacccaaat tcaaacaaaa
           421 aaaagcaata aaaaaaccag atcttaa.

Figure 7

```
1 Consensus seq  127 TCTAAAACTCCAAAA[          ]ATGTTGATCAAGATGAAC 176
2 Consensus seq  116 TCTAAAACTCCAAAA[          ]ATGTTGATCAAGATGAAC 165
3 Consensus seq  118 TCTAAAACTCCAAAA[          ]ATGTTGATCAAGATGAAC 167
4 Consensus seq  127 TCTAAAACTCCAAAA[          ]ATGTTGATCAAGATGAAC 176
5 Consensus seq   98 TCTAAAACTCCAAAA[          ]ATGTTGATCAAGATGAAC 147
6 Consensus seq  120 TCTAAAACTCCAAAA[          ]ATGTTGATCAAGATGAAC 169
7 Consensus seq  120 TCTAAAACTCCAAAA[          ]ATGTTGATCAAGATGAAC 169
8 Consensus seq  120 TCTAAAACTCCAAAA[          ]ATGTTGATCAAGATGAAC 169
9 Consensus seq   97 TCTAAAACTCCAAAA[          ]ATGTTGATCAAGATGAAC 146
10 Consensus se  120 TCTAAAACTCCAAAA[          ]ATGTTGATCAAGATGAAC 169
11 Consensus se  122 TCTAAAACTCCAAAA[          ]ATGTTGATCAAGATGAAC 171
12 Consensus se  120 TCTAAAACTCCAAAA[          ]ATGTTGATCAAGATGAAC 169
+ve MG 2 consen 127 TCTAAAACTCCAAAA[          ]ATGTTGATCAAGATGAAC 176
+ve MG 3 consen 120 TCTAAAACTCCAAAA[          ]ATGTTGATCAAGATGAAC 169
+ve MG 5 consen 120 TCTAAAACTCCAAAA[          ]ATGTTGATCAAGATGAAC 169
+ve MG 6 consen 127 TCTAAAACTCCAAAA[          ]ATGTTGATCAAGATGAAC 176
MG219 +-100bp   151 TCTAAAACTCCAAAA[          ]ATGTTGATCAAGATGAAC 200
                    ************************************************
                              Binding site for probe
                                  (SEQ ID NO: 3)

1 Consensus seq  177 TTAGTTTAACAACTACTGCAGTTGAACTTAAAAAGAGTGATGAACAAAAA 226
2 Consensus seq  166 TTAGTTTAACAACTACTGCAGTTGAACTTAAAAAGAGTGATGAACAAAAA 215
3 Consensus seq  168 TTAGTTTAACAACTACTGCAGTTGAACTTAAAAAGAGTGATGAACAAAAA 217
4 Consensus seq  177 TTAGTTTAACAACTACTGCAGTTGAACTTAAAAAGAGTGATGAACAAAAA 226
5 Consensus seq  148 TTAGTTTAACAACTACTGCAGTTGAACTTAAAAAGAGTGATGAACAAAAA 197
6 Consensus seq  170 TTAGTTTAACAACTACTGCAGTTGAACTTAAAAAGAGTGATGAACAAAAA 219
7 Consensus seq  170 TTAGTTTAACAACTACTGCAGTTGAACTTAAAAAGAGTGATGAACAAAAA 219
8 Consensus seq  170 TTAGTTTAACAACTACTGCAGTTGAACTTAAAAAGAGTGATGAACAAAAA 219
9 Consensus seq  147 TTAGTTTAACAACTACTGCAGTTGAACTTAAAAAGAGTGATGAACAAAAA 196
10 Consensus se  170 TTAGTTTAACAACTACTGCAGTTGAACTTAAAAAGAGTGATGAACAAAAA 219
11 Consensus se  172 TTAGTTTAACAACTACTGCAGTTGAACTTAAAAAGAGTGATGAACAAAAA 221
12 Consensus se  170 TTAGTTTAACAACTACTGCAGTTGAACTTAAAAAGAGTGATGAACAAAAA 219
+ve MG 2 consen 177 TTAGTTTAACAACTACTGCAGTTGAACTTAAAAAGAGTGATGAACAAAAA 226
+ve MG 3 consen 170 TTAGTTTAACAACTACTGCAGTTGAACTTAAAAAGAGTGATGAACAAAAA 219
+ve MG 5 consen 170 TTAGTTTAACAACTACTGCAGTTGAACTTAAAAAGAGTGATGAACAAAAA 219
+ve MG 6 consen 177 TTAGTTTAACAACTACTGCAGTTGAACTTAAAAAGAGTGATGAACAAAAA 226
MG219 +-100bp   201 TTAGTTTAACAACTACTGCAGTTGAACTTAAAAAGAGTGATGAACAAAAA 250
                    **************************************************

1 Consensus seq  227 CCTGTTGCCATTAAAAGTAGTGACTTTATTGGTCATGAAGAGTTAATCTC 276
2 Consensus seq  216 CCTGTTGCCATTAAAAGTAGTGACTTTATTGGTCATGAAGAGTTAATCTC 265
3 Consensus seq  218 CCTGTTGCCATTAAAAGTAGTGACTTTATTGGTCATGAAGAGTTAATCTC 267
4 Consensus seq  227 CCTGTTGCCATTAAAAGTAGTGACTTTATTGGTCATGAAGAGTTAATCTC 276
5 Consensus seq  198 CCTGTTGCCATTAAAAGTAGTGACTTTATTGGTCATGAAGAGTTAATCTC 247
6 Consensus seq  220 CCTGTTGCCATTAAAAGTAGTGACTTTATTGGTCATGAAGAGTTAATCTC 269
7 Consensus seq  220 CCTGTTGCCATTAAAAGTAGTGACTTTATTGGTCATGAAGAGTTAATCTC 269
8 Consensus seq  220 CCTGTTGCCATTAAAAGTAGTGACTTTATTGGTCATGAAGAGTTAATCTC 269
9 Consensus seq  197 CCTGTTGCCATTAAAAGTAGTGACTTTATTGGCCATGAAGAATTAATCTC 246
10 Consensus se  220 CCTGTTGCCATTAAAAGTAGTGACTTTATTGGTCATGAAGAGTTAATCTC 269
11 Consensus se  222 CCTGTTGCCATTAAAAGTAGTGACTTTATTGGCCATGAAGAATTAATCTC 271
12 Consensus se  220 CCTGTTGCCATTAAAAGTAGTGACTTTATTGGTCATGAAGAGTTAATCTC 269
+ve MG 2 consen 227 CCTGTTGCCATTAAAAGTAGTGACTTTATTGGTCATGAAGAGTTAATCTC 276
+ve MG 3 consen 220 CCTGTTGCCATTAAAAGTAGTGACTTTATTGGTCATGAAGAGTTAATCTC 269
+ve MG 5 consen 220 CCTGTTGCCATTAAAAGTAGTGACTTTATTGGTCATGAAGAGTTAATCTC 269
+ve MG 6 consen 227 CCTGTTGCCATTAAAAGTAGTGACTTTATTGGCCATGAAGAATTAATCTC 276
MG219 +-100bp   251 CCTGTTGCCATTAAAAGTAGTGACTTTATTGGTCATGAAGAGTTAATCTC 300
                    ******************************** ******* *********
```

Figure 7
(CONT.)

```
 1 Consensus seq 277 TGTTCCAGTTTTA[......]ATTGATCAAC 326
 2 Consensus seq 266 TGTTCCAGTTTTA[......]ATTGATCAAC 315
 3 Consensus seq 268 TGTTCCAGTTTTA[......]ATTGATCAAC 317
 4 Consensus seq 277 TGTTCCAGTTTTA[......]ATTGATCAAC 326
 5 Consensus seq 248 TGTTCCAGTTTTA[......]ATTGATCAAC 297
 6 Consensus seq 270 TGTTCCAGTTTTA[......]ATTGATCAAC 319
 7 Consensus seq 270 TGTTCCAGTTTTA[......]ATTGATCAAC 319
 8 Consensus seq 270 TGTTCCAGTTTTA[......]ATTGATCAAC 319
 9 Consensus seq 247 TGTTCAGTTTTA[......]ATTGACCAAC 296
10 Consensus se  270 TGTTCCAGTTTTA[......]ATTGATCAAC 319
11 Consensus se  272 TGTTCCAGTTTTA[......]ATTGACCAAC 321
12 Consensus se  270 TGTTCCAGTTTTA[......]ATTGATCAAC 319
+ve MG 2 consen 277 TGTTCCAGTTTTA[......]ATTGATCAAC 326
+ve MG 3 consen 270 TGTTCCAGTTTTA[......]ATTGATCAAC 319
+ve MG 5 consen 270 TGTTCCAGTTTTA[......]ATTGATCAAC 319
+ve MG 6 consen 277 TGTTCCAGTTTTA[......]ATTGACCAAC 326
MG219 +-100bp   301 TGTTCCAGTTTTA[......]ATTGATCAAC 350
                    *************           **********  ****
                    Binding site for reverse primer
                    (SEQ ID NO: 5)

1 Consensus seq 327 CAGCAGTTATTCCTCCAGTTAAAGCAAAACCAAAAGCAACTAAAAAGAAA 376
 2 Consensus seq 316 CAGCAGTTATTCCTCCAGTTAAAGCAAAACCAAAAGCAACTAAAAAGAAA 365
 3 Consensus seq 318 CAGCAGTTATTCCTCCAGTTAAAGCAAAACCAAAAGCAACTAAAAAGAAA 367
 4 Consensus seq 327 CAGCAGTTATTCCTCCAGTTAAAGCAAAACCAAAAGCAACTAAAAAGAAA 376
 5 Consensus seq 298 CAGCAGTTATTCCTCCAGTTAAAGCAAAACCAAAAGCAACTAAAAAGAAA 347
 6 Consensus seq 320 CAGCAGTTATTCCTCCAGTTAAAGCAAAACCAAAAGCAACTAAAAAGAAA 369
 7 Consensus seq 320 CAGCAGTTATTCCTCCAGTTAAAGCAAAACCAAAAGCAACTAAAAAGAAA 369
 8 Consensus seq 320 CAGCAGTTATTCCTCCAGTTAAAGCAAAACCAAAAGCAACTAAAAAGAAA 369
 9 Consensus seq 297 CAGTAGTTATTCTCCAGTTAAAGCAAAACCAAAAGCAACTAAAAAGAAA 346
10 Consensus se  320 CAGCAGTTATTCCTCCAGTTAAAGCAAAACCAAAAGCAACTAAAAAGAAA 369
11 Consensus se  322 CAGTAGTTATTCTCCAGTTAAAGCAAAACCAAAAGCAACTAAAAAGAAA 371
12 Consensus se  320 CAGCAGTTATTCCTCCAGTTAAAGCAAAACCAAAAGCAACTAAAAAGAAA 369
+ve MG 2 consen 327 CAGCAGTTATTCCTCCAGTTAAAGCAAAACCAAAAGCAACTAAAAAGAAA 376
+ve MG 3 consen 320 CAGCAGTTATTCCTCCAGTTAAAGCAAAACCAAAAGCAACTAAAAAGAAA 369
+ve MG 5 consen 320 CAGCAGTTATTCCTCCAGTTAAAGCAAAACCAAAAGCAACTAAAAAGAAA 369
+ve MG 6 consen 327 CAGCAGTTATTCCTCCAGTTAAAGCAAAACCAAAAGCAACTAAAAAGAAA 376
MG219 +-100bp   351 CAGCAGTTATTCCTCCAGTTAAAGCAAAACCAAAAGCAACTAAAAAGAAA 400
                    *** ******* *** *********************************

1 Consensus seq 377 ACTCCTGTTAAATCAAAACCAACTAGTAAATCAACTAAACAAACAAAACC 426
 2 Consensus seq 366 ACTCCTGTTAAATCAAAACCAACTAGTAAATCAACTAAACAAACAAAACC 415
 3 Consensus seq 368 ACTCCTGTTAAATCAAAACCAACTAGTAAATCAACTAAACAAACAAAACC 417
 4 Consensus seq 377 ACTCCTGTTAAATCAAAACCAACTAGTAAATCAACTAAACAAACAAAACC 426
 5 Consensus seq 348 ACTCCTGTTAAATCAAAACCAACTAGTAAATCAACTAAACAAACAAAACC 397
 6 Consensus seq 370 ACTCCTGTTAAATCAAAACCAACTAGTAAATCAACTAAACAAACAAAACC 419
 7 Consensus seq 370 ACTCCTGTTAAATCAAAACCAACTAGTAAATCAACTAAACAAACAAAACC 419
 8 Consensus seq 370 ACTCCTGTTAAATCAAAACCAACTAGTAAATCAACTAAACAAACAAAACC 419
 9 Consensus seq 347 ACTCCTGTTAAATCAAAACCAACTAGTAAATCAACTAAACAAACAAAACC 396
10 Consensus se  370 ACTCCTGTTAAATCAAAACCAACTAGTAAATCAACTAAACAAACAAAACC 419
11 Consensus se  372 ACTCCTGTTAAATCAAAACCAACTAATAAATCAACTAAACAAACAAAACC 421
12 Consensus se  370 ACTCCTGTTAAATCAAAACCAACTAGTAAATCAACTAAACAAACAAAACC 419
+ve MG 2 consen 377 ACTCCTGTTAAATCAAAACCAACTAGTAAATCAACTAAACAAACAAAACC 426
+ve MG 3 consen 370 ACTCCTGTTAAATCAAAACCAACTAGTAAATCAACTAAACAAACAAAACC 419
+ve MG 5 consen 370 ACTCCTGTTAAATCAAAACCAACTAGTAAATCAACTAAACAAACAAAACC 419
+ve MG 6 consen 377 ACTCCTGTTAAATCAAAACCAACTAATAAATCAACTAAACAAACAAAACC 426
MG219 +-100bp   401 ACTCCTGTTAAATCAAAACCAACTAGTAAATCAACTAAACAAACAAAACC 450
                    ************************* ***********************
```

```
1 Consensus seq   546 ACAGTAGTTTTAACTAAAAACTGGAAAGGAATAGGAAGAACTACCTGGGG 595
2 Consensus seq   535 ACAGTAGTTTTAACTAAAAACTGGAAAGGAATAGGAAGAACTACCTGGGG 584
3 Consensus seq   537 ACAGTAGTTTTAACTAAAAACTGGAAAGGAATAGGAAGAACTACCTGGGG 586
4 Consensus seq   546 ACAGTAGTTTTAACTAAAAACTGGAAAGGAATAGGAAGAACTACCTGGGG 595
5 Consensus seq   517 ACAGTAGTTTTAACTAAAAACTGGAAAGGAATAGGAAGAACTACCTGGGG 566
6 Consensus seq   539 ACAGTAGTTTTAACTAAAAACTGGAAAGGAATAGGAAGAACTACCTGG   586
7 Consensus seq   539 ACAGTAGTTTTAACTAAAAACTGGAAAGGAATAGGAAGAACTACCTG    586
8 Consensus seq   539 ACAGTAGTTTTAACTAAAAACTGGAAAGGAATAGGAAGAACTACCTGGGG 588
9 Consensus seq   547 ACAGTAGTTTTAACTAAAAACTGGAAAGGAATAGGAAGAACTACCTGG   594
10 Consensus se   539 ACAGTAGTTTTAACTAAAAACTGGAAAGGAATAGGAAGAACTACCTG    585
11 Consensus se   571 ACAGTAGTTTTAACTAAAAACTGGAAAGGAATAGGAAGAACTACC      615
12 Consensus se   539 ACAGTAGTTTTAACTAAAAACTGGAAAGGAATAGGAAGAACTACCTGGGG 588
+ve MG 2 consen  546 ACAGTAGTTTTAACTAAAAACTGGAAAGGAATAGGAAGAACTACCTGGGG 595
+ve MG 3 consen  539 ACAGTAGTTTTAACTAAAAACTGGAAAGGAATAGGAAGAACTACCTGGGG 589
+ve MG 5 consen  539 ACAGTAGTTTTAACTAAAAACTGGAAAGGAATAGGAAGAACTACCTGGGG 588
+ve MG 6 consen  576 ACAGTAGTTTTAACTAAAAACTGGAAAGGAATAGGAAGAACTACCTGGGG 625
MG219 +-100bp    570 ACAGTAGTTTTAACTAAAAACTGGAAAGGAATA████████████████  619
                     *********************************
                                                     Binding site for sequencing
                                                     Primer (SEQ ID NO: 20)

1 Consensus seq   596 TTAA   599
2 Consensus seq   585 T      585
3 Consensus seq   587 T      587
4 Consensus seq   596 T      596
5 Consensus seq   567 TT     568
6 Consensus seq   587         586
7 Consensus seq   587         586
8 Consensus seq   589 TTAAT  593
9 Consensus seq   595         594
10 Consensus se   586         585
11 Consensus se   616         615
12 Consensus se   589         588
+ve MG 2 consen  596 TTAAT  600
+ve MG 3 consen  589         589
+ve MG 5 consen  589 TTAAT  593
+ve MG 6 consen  626 T      626
MG219 +-100bp    620 █████  647
```

Similarity Scores (%)

| | 1 | 2 | 3 | 4 | 5 | 6 | 7 | 8 | 9 | 10 | 11 | 12 | +veMG2 | +veMG3 | +veMG5 | +veMG6 | G37 |
|---|---|---|---|---|---|---|---|---|---|---|---|---|---|---|---|---|---|
| 1 | | 100.0 | 100.0 | 100.0 | 100.0 | 100.0 | 100.0 | 100.0 | 93.1 | 100.0 | 93.2 | 100.0 | 99.8 | 100.0 | 100.0 | 93.2 | 100.0 |
| 2 | 100.0 | | 100.0 | 100.0 | 100.0 | 100.0 | 100.0 | 100.0 | 93.1 | 100.0 | 93.2 | 100.0 | 99.8 | 100.0 | 100.0 | 93.2 | 100.0 |
| 3 | 100.0 | 100.0 | | 100.0 | 100.0 | 100.0 | 100.0 | 100.0 | 93.1 | 100.0 | 93.2 | 100.0 | 99.8 | 100.0 | 100.0 | 93.2 | 100.0 |
| 4 | 100.0 | 100.0 | 100.0 | | 100.0 | 100.0 | 100.0 | 100.0 | 93.1 | 100.0 | 93.2 | 100.0 | 99.8 | 100.0 | 100.0 | 93.2 | 100.0 |
| 5 | 100.0 | 100.0 | 100.0 | 100.0 | | 100.0 | 100.0 | 100.0 | 93.1 | 100.0 | 93.2 | 100.0 | 99.8 | 100.0 | 100.0 | 93.2 | 100.0 |
| 6 | 100.0 | 100.0 | 100.0 | 100.0 | 100.0 | | 100.0 | 100.0 | 93.1 | 100.0 | 93.2 | 100.0 | 99.8 | 100.0 | 100.0 | 93.2 | 100.0 |
| 7 | 100.0 | 100.0 | 100.0 | 100.0 | 100.0 | 100.0 | | 100.0 | 93.1 | 100.0 | 93.2 | 100.0 | 99.8 | 100.0 | 100.0 | 93.2 | 100.0 |
| 8 | 100.0 | 100.0 | 100.0 | 100.0 | 100.0 | 100.0 | 100.0 | | 93.1 | 100.0 | 93.2 | 100.0 | 99.8 | 100.0 | 100.0 | 93.2 | 100.0 |
| 9 | 93.1 | 93.1 | 93.1 | 93.1 | 93.1 | 93.1 | 93.1 | 93.1 | | 93.1 | 99.8 | 93.1 | 92.9 | 93.1 | 93.1 | 99.8 | 93.1 |
| 10 | 100.0 | 100.0 | 100.0 | 100.0 | 100.0 | 100.0 | 100.0 | 100.0 | 93.1 | | 93.2 | 100.0 | 99.8 | 100.0 | 100.0 | 93.2 | 100.0 |
| 11 | 93.2 | 93.2 | 93.2 | 93.2 | 93.2 | 93.2 | 93.2 | 93.2 | 99.8 | 93.2 | | 93.2 | 93.1 | 93.2 | 93.2 | 100.0 | 93.2 |
| 12 | 100.0 | 100.0 | 100.0 | 100.0 | 100.0 | 100.0 | 100.0 | 100.0 | 93.1 | 100.0 | 93.1 | | 99.8 | 100.0 | 100.0 | 93.1 | 100.0 |
| +ve MG 2 | 99.8 | 99.8 | 99.8 | 99.8 | 99.8 | 99.8 | 99.8 | 99.8 | 92.9 | 99.8 | 93.1 | 99.8 | | 99.8 | 99.8 | 93.1 | 99.8 |
| +ve MG 3 | 100.0 | 100.0 | 100.0 | 100.0 | 100.0 | 100.0 | 100.0 | 100.0 | 93.1 | 100.0 | 93.2 | 100.0 | 99.8 | | 100.0 | 93.2 | 100.0 |
| +ve MG 5 | 100.0 | 100.0 | 100.0 | 100.0 | 100.0 | 100.0 | 100.0 | 100.0 | 93.1 | 100.0 | 93.2 | 100.0 | 99.8 | 100.0 | | 93.2 | 100.0 |
| +ve MG 6 | 93.2 | 93.2 | 93.2 | 93.2 | 93.2 | 93.2 | 93.2 | 93.2 | 99.8 | 93.2 | 100.0 | 93.2 | 93.1 | 93.2 | 93.2 | | 93.2 |
| G37 | 100.0 | 100.0 | 100.0 | 100.0 | 100.0 | 100.0 | 100.0 | 100.0 | 93.1 | 100.0 | 93.2 | 100.0 | 99.8 | 100.0 | 100.0 | 93.2 | |

Identity Scores (%)

SEQUENCE LISTING

```
<160> NUMBER OF SEQ ID NOS: 48

<210> SEQ ID NO 1
<211> LENGTH: 446
<212> TYPE: DNA
<213> ORGANISM: Mycoplasma genitalium

<400> SEQUENCE: 1
atgcgcacca gttacttgaa aaaatacccc ataatgaata gtgatagtga tctaaaactc      60
caaaaggtgt gatcgagcgg catgtttgatc aagatgaact tagtttaaca actactgcag    120
ttgaacttaa aaagagtgat gaacaaaaac ctgttgccat taaaagtagt gactttattg    180
gtcatgaaga gttaatctct gttccagttt tactaatccc aaccctgtt gttaaagaga      240 ttgatcaacc agcagttatt cctccagtta aagcaaaacc aaaagcaact aaaaagaaaa    300
ctcctgttaa atcaaaacca actagtaaat caactaaaca aacaaaacct aaacaatcca    360
agcccaaatc aaaacaagtt caacaaacca aagctaaacc aacccaaatt caacaaaaaa    420
aaagcaataa aaaaaccaga tcttaa                                        446

<210> SEQ ID NO 2
<211> LENGTH: 148
<212> TYPE: PRT
<213> ORGANISM: Mycoplasma genitalium

<400> SEQUENCE: 2

Met Arg Thr Ser Tyr Leu Lys Lys Ile Pro Ile Met Asn Ser Asp Ser
1               5                   10                  15

Asp Leu Lys Leu Gln Lys Val Trp Ile Glu Arg His Val Asp Gln Asp
                20                  25                  30

Glu Leu Ser Leu Thr Thr Thr Ala Val Glu Leu Lys Lys Ser Asp Glu
            35                  40                  45

Gln Lys Pro Val Ala Ile Lys Ser Ser Asp Phe Ile Gly His Glu Glu
        50                  55                  60

Leu Ile Ser Val Pro Val Leu Leu Ile Pro Thr Pro Val Val Lys Glu
65                  70                  75                  80

Ile Asp Gln Pro Ala Val Ile Pro Pro Val Lys Ala Lys Pro Lys Ala
                85                  90                  95

Thr Lys Lys Lys Thr Pro Val Lys Ser Lys Pro Thr Ser Lys Ser Thr
                100                 105                 110

Lys Gln Thr Lys Pro Lys Gln Ser Lys Pro Lys Ser Lys Gln Val Gln
            115                 120                 125

Gln Thr Lys Ala Lys Pro Thr Gln Ile Gln Thr Lys Lys Ser Asn Lys
```

```
            130                 135                 140
Lys Thr Arg Ser
145

<210> SEQ ID NO 3
<211> LENGTH: 17
<212> TYPE: DNA
<213> ORGANISM: Artificial Sequence
<220> FEATURE:
<223> OTHER INFORMATION: Probe

<400> SEQUENCE: 3
ggtgtggatc gagcggc                                                  17

<210> SEQ ID NO 4
<211> LENGTH: 29
<212> TYPE: DNA
<213> ORGANISM: Artificial Sequence
<220> FEATURE:
<223> OTHER INFORMATION: Forward Primer

<400> SEQUENCE: 4
gacagttcat tatgcgcacc agttacttg                                     29

<210> SEQ ID NO 5
<211> LENGTH: 27
<212> TYPE: DNA
<213> ORGANISM: Artificial Sequence
<220> FEATURE:
<223> OTHER INFORMATION: Reverse Primer

<400> SEQUENCE: 5
ctctttaaca caggggttg ggattag                                        27

<210> SEQ ID NO 6
<211> LENGTH: 60
<212> TYPE: DNA
<213> ORGANISM: Mycoplasma genitalium

<400> SEQUENCE: 6
cccgtcctgt tttcaaaagt aatttgccac cgaaactaag taaggatgac atagttcatt   60

<210> SEQ ID NO 7
<211> LENGTH: 53
<212> TYPE: DNA
<213> ORGANISM: Mycoplasma genitalium

<400> SEQUENCE: 7
tctggttttt ttagtgttaa caacagtagt tttaactaaa aactggaaag gaa          53

<210> SEQ ID NO 8
<211> LENGTH: 29
<212> TYPE: DNA
<213> ORGANISM: Artificial sequence
<220> FEATURE:
<223> OTHER INFORMATION: Forward Primer

<400> SEQUENCE: 8
catagttcat tatgcgcacc agttacttg                                     29

<210> SEQ ID NO 9
<211> LENGTH: 23
<212> TYPE: DNA
<213> ORGANISM: artificial sequence
<220> FEATURE:
```

```
<223> OTHER INFORMATION: Primer

<400> SEQUENCE: 9
ccacttaact ttattacccg tcc                                              23

<210> SEQ ID NO 10
<211> LENGTH: 53
<212> TYPE: DNA
<213> ORGANISM: Artificial sequence
<220> FEATURE:
<223> OTHER INFORMATION: Primer

<400> SEQUENCE: 10
tgttttcaaa agtaatttgc caccgaaact aagtaaggat gacatagttc att              53

<210> SEQ ID NO 11
<211> LENGTH: 50
<212> TYPE: DNA
<213> ORGANISM: Artificial sequence
<220> FEATURE:
<223> OTHER INFORMATION: Primer

<400> SEQUENCE: 11
atgcgcacca gttacttgaa aaaataccc ataatgaata gtgatagtga                   50

<210> SEQ ID NO 12
<211> LENGTH: 50
<212> TYPE: DNA
<213> ORGANISM: Artificial sequence
<220> FEATURE:
<223> OTHER INFORMATION: Primer

<400> SEQUENCE: 12
tctaaaactc caaaggtgt ggatcgagcg gcatgttgat caagatgaac                   50

<210> SEQ ID NO 13
<211> LENGTH: 50
<212> TYPE: DNA
<213> ORGANISM: Artificial sequence
<220> FEATURE:
<223> OTHER INFORMATION: Primer

<400> SEQUENCE: 13
ttagtttaac aactactgca gttgaactta aaaagagtga tgaacaaaaa                  50

<210> SEQ ID NO 14
<211> LENGTH: 50
<212> TYPE: DNA
<213> ORGANISM: Artificial sequence
<220> FEATURE:
<223> OTHER INFORMATION: Primer

<400> SEQUENCE: 14
cctgttgcca ttaaaagtag tgactttatt ggtcatgaag agttaatctc                  50

<210> SEQ ID NO 15
<211> LENGTH: 50
<212> TYPE: DNA
<213> ORGANISM: Artificial sequence
<220> FEATURE:
<223> OTHER INFORMATION: Primer

<400> SEQUENCE: 15
tgttccagtt ttactaatcc caaccectgt tgttaaagag attgatcaac                  50
```

<210> SEQ ID NO 16
<211> LENGTH: 50
<212> TYPE: DNA
<213> ORGANISM: Artificial sequence
<220> FEATURE:
<223> OTHER INFORMATION: Primer

<400> SEQUENCE: 16
cagcagttat tcctccagtt aaagcaaaac caaaagcaac taaaaagaaa        50

<210> SEQ ID NO 17
<211> LENGTH: 50
<212> TYPE: DNA
<213> ORGANISM: Artificial sequence
<220> FEATURE:
<223> OTHER INFORMATION: Primer

<400> SEQUENCE: 17
actcctgtta aatcaaaacc aactagtaaa tcaactaaac aaacaaaacc        50

<210> SEQ ID NO 18
<211> LENGTH: 50
<212> TYPE: DNA
<213> ORGANISM: Artificial sequence
<220> FEATURE:
<223> OTHER INFORMATION: Primer

<400> SEQUENCE: 18
taaacaatcc aagcccaaat caaacaagt tcaacaaacc aaagctaaac        50

<210> SEQ ID NO 19
<211> LENGTH: 50
<212> TYPE: DNA
<213> ORGANISM: Artificial sequence
<220> FEATURE:
<223> OTHER INFORMATION: Primer

<400> SEQUENCE: 19
caacccaaat tcaaacaaaa aaaagcaata aaaaaaccag atcttaatct        50

<210> SEQ ID NO 20
<211> LENGTH: 23
<212> TYPE: DNA
<213> ORGANISM: Artificial sequence
<220> FEATURE:
<223> OTHER INFORMATION: Primer

<400> SEQUENCE: 20
gattaacccc aggtagttct tcc        23

<210> SEQ ID NO 21
<211> LENGTH: 55
<212> TYPE: DNA
<213> ORGANISM: Artificial sequence
<220> FEATURE:
<223> OTHER INFORMATION: Primer

<400> SEQUENCE: 21
tattcctttc cagtttttag ttaaaactac tgttgttaac actaaaaaaa ccaga        55

<210> SEQ ID NO 22
<211> LENGTH: 50
<212> TYPE: DNA
<213> ORGANISM: Artificial sequence
<220> FEATURE:
<223> OTHER INFORMATION: Primer

<400> SEQUENCE: 22
ttaagatctg gtttttttat tgcttttttt tgtttgaatt tgggttggtt                50

<210> SEQ ID NO 23
<211> LENGTH: 50
<212> TYPE: DNA
<213> ORGANISM: Artificial sequence
<220> FEATURE:
<223> OTHER INFORMATION: Primer

<400> SEQUENCE: 23
tagctttggt ttgttgaact tgttttgatt tgggcttgga ttgtttaggt                50

<210> SEQ ID NO 24
<211> LENGTH: 50
<212> TYPE: DNA
<213> ORGANISM: Artificial sequence
<220> FEATURE:
<223> OTHER INFORMATION: Primer

<400> SEQUENCE: 24
tttgtttgtt tagttgattt actagttggt tttgatttaa caggagtttt                50

<210> SEQ ID NO 25
<211> LENGTH: 50
<212> TYPE: DNA
<213> ORGANISM: Artificial sequence
<220> FEATURE:
<223> OTHER INFORMATION: Primer

<400> SEQUENCE: 25 cttttttagtt gcttttggtt ttgctttaac tggaggaata actgctggtt               50

<210> SEQ ID NO 26
<211> LENGTH: 50
<212> TYPE: DNA
<213> ORGANISM: Artificial sequence
<220> FEATURE:
<223> OTHER INFORMATION: Primer

<400> SEQUENCE: 26
gatcaatctc tttaacaaca ggggttggga ttagtaaaac tggaacagag                50

<210> SEQ ID NO 27
<211> LENGTH: 50
<212> TYPE: DNA
<213> ORGANISM: Artificial sequence
<220> FEATURE:
<223> OTHER INFORMATION: Primer

<400> SEQUENCE: 27
attaactctt catgaccaat aaagtcacta cttttaatgg caacaggttt                50

<210> SEQ ID NO 28
<211> LENGTH: 50
<212> TYPE: DNA
<213> ORGANISM: Artificial sequence
<220> FEATURE:
<223> OTHER INFORMATION: Primer

<400> SEQUENCE: 28
ttgttcatca ctcttttttaa gttcaactgc agtagttgtt aaactaagtt               50

<210> SEQ ID NO 29
<211> LENGTH: 50

-continued

<212> TYPE: DNA
<213> ORGANISM: Artificial sequence
<220> FEATURE:
<223> OTHER INFORMATION: Primer

<400> SEQUENCE: 29
catcttgatc aacatgccgc tcgatccaca cctttggag ttttagatca    50

<210> SEQ ID NO 30
<211> LENGTH: 50
<212> TYPE: DNA
<213> ORGANISM: Artificial sequence
<220> FEATURE:
<223> OTHER INFORMATION: Primer

<400> SEQUENCE: 30
ctatcactat tcattatggg tatttttttc aagtaactgg tgcgcataat    50

<210> SEQ ID NO 31
<211> LENGTH: 29
<212> TYPE: DNA
<213> ORGANISM: Artificial sequence
<220> FEATURE:
<223> OTHER INFORMATION: Primer

<400> SEQUENCE: 31
catagttcat tatgcacacc agttacttg                           29

<210> SEQ ID NO 32
<211> LENGTH: 599
<212> TYPE: DNA
<213> ORGANISM: Artificial Sequence
<220> FEATURE:
<223> OTHER INFORMATION: DNA Sequence including Mg219 gene

<400> SEQUENCE: 32
ccacttaact ttattacccg tcctgttttc aaaagtaatt tgccaccgaa actaagtaag    60
gatgacatag ttcattatgc gcaccagtta cttgaaaaaa atacccataa tgaatagtga   120
tagtgatcta aaactccaaa aggtgtggat cgagcggcat gttgatcaag atgaacttag   180
tttaacaact actgcagttg aacttaaaaa gagtgatgaa caaaaacctg ttgccattaa   240
aagtagtgac tttattggtc atgaagagtt aatctctgtt ccagttttac taatcccaac   300
ccctgttgtt aaagagattg atcaaccagc agttattcct ccagttaaag caaaaccaaa   360
agcaactaaa aagaaaactc ctgttaaatc aaaaccaact agtaaatcaa ctaaacaaac   420
aaaacctaaa caatccaagc ccaaatcaaa acaagttcaa caaaccaaag ctaaaccaac   480
ccaaattcaa acaaaaaaaa gcaataaaaa aaccagatct taatctggtt tttttagtgt   540
taacaacagt agttttaact aaaaactgga aaggaatagg aagaactacc tggggttaa    599

<210> SEQ ID NO 33
<211> LENGTH: 585
<212> TYPE: DNA
<213> ORGANISM: Artificial sequence
<220> FEATURE:
<223> OTHER INFORMATION: DNA sequence inlduing Mg219 gene

<400> SEQUENCE: 33
tattacccgt cctgttttca aaagtaattt gccaccgaaa ctaagtaagg atgacatagt    60
tcattatgcg caccagttac ttgaaaaaaa tacccataat gaatagtgat agtgatctaa   120
aactccaaaa ggtgtggatc gagcggcatg ttgatcaaga tgaacttagt ttaacaacta   180

```
ctgcagttga acttaaaaag agtgatgaac aaaaacctgt tgccattaaa agtagtgact    240
ttattggtca tgaagagtta atctctgttc cagttttact aatcccaacc cctgttgtta    300
aagagattga tcaaccagca gttattcctc cagttaaagc aaaaccaaaa gcaactaaaa    360
agaaaactcc tgttaaatca aaccaacta gtaaatcaac taaacaaaca aaacctaaac     420
aatccaagcc caaatcaaaa caagttcaac aaaccaaagc taaaccaacc caaattcaaa    480 caaaaaaag caataaaaaa accagatctt aatctggttt ttttagtgtt aacaacagta     540
gttttaacta aaaactggaa aggaatagga agaactacct ggggt                    585

<210> SEQ ID NO 34
<211> LENGTH: 587
<212> TYPE: DNA
<213> ORGANISM: Artificial sequence
<220> FEATURE:
<223> OTHER INFORMATION: DNA sequence including Mg219 gene

<400> SEQUENCE: 34
tttattaccc gtcctgtttt caaaagtaat ttgccaccga aactaagtaa ggatgacata     60
gttcattatg cgcaccagtt acttgaaaaa atacccata atgaatagtg atagtgatct     120
aaaactccaa aaggtgtgga tcgagcggca tgttgatcaa gatgaactta gtttaacaac    180
tactgcagtt gaacttaaaa agagtgatga caaaaacct gttgccatta aaagtagtga    240
ctttattggt catgaagagt taatctctgt tccagtttta ctaatcccaa ccctgttgt     300 taaagagatt gatcaaccag cagttattcc tccagttaaa gcaaaaccaa agcaactaa    360 aaagaaaact cctgttaaat caaaaccaac tagtaaatca actaaacaaa caaaacctaa    420
acaatccaag cccaaatcaa aacaagttca acaaaccaaa gctaaaccaa cccaaattca    480
aacaaaaaaa agcaataaaa aaaccagatc ttaatctggt tttttagtg ttaacaacag     540 tagttttaac taaaaactgg aaaggaatag gaagaactac ctggggt                  587

<210> SEQ ID NO 35
<211> LENGTH: 596
<212> TYPE: DNA
<213> ORGANISM: Artificial sequence
<220> FEATURE:
<223> OTHER INFORMATION: DNA sequence including Mg219 gene

<400> SEQUENCE: 35
ccacttaact ttattacccg tcctgttttc aaaagtaatt tgccaccgaa actaagtaag     60
gatgacatag ttcattatgc gcaccagtta cttgaaaaaa atacccataa tgaatagtga    120
tagtgatcta aaactccaaa aggtgtggat cgagcggcat gttgatcaag atgaacttag    180
tttaacaact actgcagttg aacttaaaaa gagtgatgaa caaaaacctg ttgccattaa    240
aagtagtgac tttattggtc atgaagagtt aatctctgtt ccagttttac taatcccaac    300
ccctgttgtt aaagagattg atcaaccagc agttattcct ccagttaaag caaaaccaaa    360
agcaactaaa aagaaaactc ctgttaaatc aaaaccaact agtaaatcaa ctaaacaaac    420
aaaacctaaa caatccaagc ccaaatcaaa acaagttcaa caaaccaaag ctaaaccaac    480
ccaaattcaa acaaaaaaaa gcaataaaaa aaccagatct taatctggtt ttttagtgt     540 taacaacagt agttttaact aaaaactgga aaggaatagg aagaactacc tggggt        596

<210> SEQ ID NO 36
<211> LENGTH: 568
<212> TYPE: DNA
<213> ORGANISM: Artificial Sequence
```

<220> FEATURE:
<223> OTHER INFORMATION: DNA Sequence including Mg219 gene

<400> SEQUENCE: 36

| | | |
|---|---|---|
| caaaagtaat tgccaccga aactaagtaa ggatgacata gttcattatg cgcaccagtt | 60 |
| acttgaaaaa ataccccata atgaatagtg atagtgatct aaaactccaa aaggtgtgga | 120 |
| tcgagcggca tgttgatcaa gatgaactta gtttaacaac tactgcagtt gaacttaaaa | 180 |
| agagtgatga acaaaaacct gttgccatta aaagtagtga ctttattggt catgaagagt | 240 |
| taatctctgt tccagtttta ctaatcccaa ccctgttgt aaagagatt gatcaaccag | 300 |
| cagttattcc tccagttaaa gcaaaaccaa agcaactaa aaagaaaact cctgttaaat | 360 |
| caaaaccaac tagtaaatca actaaacaaa caaaacctaa acaatccaag cccaaatcaa | 420 |
| aacaagttca acaaaccaaa gctaaaccaa cccaaattca aacaaaaaaa agcaataaaa | 480 |
| aaaccagatc ttaatctggt ttttttagtg ttaacaacag tagttttaac taaaaactgg | 540 |
| aaaggaatag gaagaactac ctggggtt | 568 |

<210> SEQ ID NO 37
<211> LENGTH: 586
<212> TYPE: DNA
<213> ORGANISM: Artificial sequence
<220> FEATURE:
<223> OTHER INFORMATION: DNA sequence including Mg219 gene

<400> SEQUENCE: 37

| | | |
|---|---|---|
| actttattac ccgtcctgtt ttcaaaagta atttgccacc gaaactaagt aaggatgaca | 60 |
| tagttcatta tgcgcaccag ttacttgaaa aaaataccca taatgaatag tgatagtgat | 120 |
| ctaaaactcc aaaaggtgtg gatcgagcgg catgttgatc aagatgaact tagtttaaca | 180 |
| actactgcag ttgaacttaa aaagagtgat gaacaaaaac ctgttgccat taaaagtagt | 240 |
| gactttattg gtcatgaaga gttaatctct gttccagttt tactaatccc aaccccctgtt | 300 |
| gttaaagaga ttgatcaacc agcagttatt cctccagtta agcaaaaacc aaaagcaact | 360 |
| aaaaagaaaa ctcctgttaa atcaaaacca actagtaaat caactaaaca aacaaaacct | 420 |
| aaacaatcca gcccaaatc aaaacaagtt caacaaacca agctaaaacc aacccaaatt | 480 |
| caaacaaaaa aaagcaataa aaaaaccaga tcttaatctg gttttttttag tgttaacaac | 540 |
| agtagtttta actaaaaact ggaaaggaat aggaagaact acctgg | 586 |

<210> SEQ ID NO 38
<211> LENGTH: 586
<212> TYPE: DNA
<213> ORGANISM: Artificial Sequence
<220> FEATURE:
<223> OTHER INFORMATION: DNA Sequence including Mg219 gene

<400> SEQUENCE: 38

| | | |
|---|---|---|
| actttattac ccgtcctgtt ttcaaaagta atttgccacc gaaactaagt aaggatgaca | 60 |
| tagttcatta tgcgcaccag ttacttgaaa aaaataccca taatgaatag tgatagtgat | 120 |
| ctaaaactcc aaaaggtgtg gatcgagcgg catgttgatc aagatgaact tagtttaaca | 180 |
| actactgcag ttgaacttaa aaagagtgat gaacaaaaac ctgttgccat taaaagtagt | 240 |
| gactttattg gtcatgaaga gttaatctct gttccagttt tactaatccc aaccccctgtt | 300 |
| gttaaagaga ttgatcaacc agcagttatt cctccagtta agcaaaaacc aaaagcaact | 360 |
| aaaaagaaaa ctcctgttaa atcaaaacca actagtaaat caactaaaca aacaaaacct | 420 |

```
aaacaatcca agcccaaatc aaaacaagtt caacaaacca aagctaaacc aacccaaatt        480
caaacaaaaa aaagcaataa aaaaaccaga tcttaatctg gttttttag tgttaacaac         540 agtagtttta actaaaaact ggaaaggaat aggaagaact acctgg                      586
```

<210> SEQ ID NO 39
<211> LENGTH: 593
<212> TYPE: DNA
<213> ORGANISM: Artificial sequence
<220> FEATURE:
<223> OTHER INFORMATION: DNA sequence including Mg219 gene

<400> SEQUENCE: 39

```
actttattac ccgtcctgtt ttcaaaagta atttgccacc gaaactaagt aaggatgaca        60
tagttcatta tgcgcaccag ttacttgaaa aaaatacccca taatgaatag tgatagtgat      120
ctaaaactcc aaaggtgtg gatcgagcgg catgttgatc aagatgaact tagtttaaca        180
actactgcag ttgaacttaa aaagagtgat gaacaaaaac ctgttgccat taaaagtagt      240
gactttattg gtcatgaaga gttaatctct gttccagttt tactaatccc aaccctgtt        300 gttaaagaga ttgatcaacc agcagttatt cctccagtta aagcaaaacc aaaagcaact      360
aaaaagaaaa ctcctgttaa atcaaaacca actagtaaat caactaaaca aacaaaacct      420
aaacaatcca agcccaaatc aaaacaagtt caacaaacca agctaaacc aacccaaatt       480 caaacaaaaa aaagcaataa aaaaaccaga tcttaatctg gttttttag tgttaacaac       540 agtagtttta actaaaaact ggaaaggaat aggaagaact acctggggtt aat             593
```

<210> SEQ ID NO 40
<211> LENGTH: 594
<212> TYPE: DNA
<213> ORGANISM: Artificial sequence
<220> FEATURE:
<223> OTHER INFORMATION: DNA sequence including Mg219 gene

<400> SEQUENCE: 40

```
aaaagtaatt tgccaccaaa actaagtaag gatgacatag ttcattatgc gcaccagtta       60
cttgaaaaaa atacccataa tgaatagtga tagtgatcta aaactccaaa aggtgtggat      120
cgagcggcat gttgatcaag atgaacttag tttaacaact actgcagttg aacttaaaaa      180
gagtgatgaa caaaaacctg ttgccattaa aagtagtgac tttattggcc atgaagaatt      240
aatctctgtt ccagttttac taatcccaac ccctgttgtt aaagagattg accaaccagt      300
agttattact ccagtaaag caaaaccaaa agcaactaaa agaaaactc ctgttaaatc       360 aaaaccaact aataaatcaa ctaaacaaac aaaacctaaa caacccaaac ccaaatcaaa      420
acaagttcaa aaaccaaag ctaaaccaaa agcaactaaa caaaccaaaa caaagccaac      480
ccaaattcaa acaaaaaaa agcaataaaa aaaccagatc ttaatctggt tttttagtg       540 ttaacaacag tagttttaac taaaaactgg aaaggaatag gaagaactac ctgg            594
```

<210> SEQ ID NO 41
<211> LENGTH: 585
<212> TYPE: DNA
<213> ORGANISM: Artificial sequence
<220> FEATURE:
<223> OTHER INFORMATION: DNA sequence including Mg219 gene

<400> SEQUENCE: 41

```
actttattac ccgtcctgtt ttcaaaagta atttgccacc gaaactaagt aaggatgaca       60
tagttcatta tgcgcaccag ttacttgaaa aaaatacccca taatgaatag tgatagtgat    120
```

```
ctaaaactcc aaaaggtgtg gatcgagcgg catgttgatc aagatgaact tagtttaaca      180
actactgcag ttgaacttaa aaagagtgat gaacaaaaac ctgttgccat taaaagtagt      240
gactttattg gtcatgaaga gttaatctct gttccagttt tactaatccc aaccctgtt       300 gttaaagaga ttgatcaacc agcagttatt cctccagtta agcaaaaacc aaaagcaact      360
aaaaagaaaa ctcctgttaa atcaaaacca actagtaaat caactaaaca aacaaaacct      420
aaacaatcca agcccaaatc aaaacaagtt caacaaacca agctaaaacc aacccaaatt      480
caaacaaaaa aaagcaataa aaaaaccaga tcttaatctg gttttttag tgttaacaac       540 agtagtttta actaaaaact ggaaaggaat aggaagaact acctg                      585
```

<210> SEQ ID NO 42
<211> LENGTH: 615
<212> TYPE: DNA
<213> ORGANISM: Artificial sequence
<220> FEATURE:
<223> OTHER INFORMATION: DNA sequence including Mg219 gene

<400> SEQUENCE: 42

```
ctactttatt acccgtcctg ttttcaaaag taatttgcca ccaaaactaa gtaaggatga       60
catagttcat tatgcgcacc agttacttga aaaaaatacc cataatgaat agtgatagtg      120
atctaaaact ccaaaaggtg tggatcgagc ggcatgttga tcaagatgaa cttagtttaa      180
caactactgc agttgaactt aaaaagagtg atgaacaaaa acctgttgcc attaaaagta      240
gtgactttat tggccatgaa gaattaatct ctgttccagt tttactaatc ccaaccctg       300 ttgttaaaga gattgaccaa ccagtagtta ttactccagt taaagcaaaa ccaaaagcaa      360
ctaaaaagaa aactcctgtt aaatcaaaac caactaataa atcaactaaa caacaaaaac      420
ctaaacaacc caaacccaaa tcaaaacaag ttcaaaaaac caaagctaaa ccaaaagcaa      480
ctaaacaaac caaaacaaag ccaacccaaa ttcaaacaaa aaaaagcaat aaaaaaacca      540
gatcttaatc tggttttttt agtgttaaca acagtagttt taactaaaaa ctggaaagga      600
ataggaagaa ctacc                                                      615
```

<210> SEQ ID NO 43
<211> LENGTH: 588
<212> TYPE: DNA
<213> ORGANISM: Artificial sequence
<220> FEATURE:
<223> OTHER INFORMATION: DNA sequence including Mg219 gene

<400> SEQUENCE: 43

```
actttattac ccgtcctgtt ttcaaaagta atttgccacc gaaactaagt aaggatgaca       60
tagttcatta tgcgcaccag ttacttgaaa aaataccca taatgaatag tgatagtgat      120
ctaaaactcc aaaaggtgtg gatcgagcgg catgttgatc aagatgaact tagtttaaca      180
actactgcag ttgaacttaa aaagagtgat gaacaaaaac ctgttgccat taaaagtagt      240
gactttattg gtcatgaaga gttaatctct gttccagttt tactaatccc aaccctgtt       300 gttaaagaga ttgatcaacc agcagttatt cctccagtta agcaaaaacc aaaagcaact      360
aaaaagaaaa ctcctgttaa atcaaaacca actagtaaat caactaaaca aacaaaacct      420
aaacaatcca agcccaaatc aaaacaagtt caacaaacca agctaaaacc aacccaaatt      480
caaacaaaaa aaagcaataa aaaaaccaga tcttaatctg gttttttag tgttaacaac       540 agtagtttta actaaaaact ggaaaggaat aggaagaact acctggg                    588
```

<210> SEQ ID NO 44
<211> LENGTH: 600
<212> TYPE: DNA
<213> ORGANISM: Artificial sequence
<220> FEATURE:
<223> OTHER INFORMATION: DNA sequence including Mg219 gene

<400> SEQUENCE: 44

```
ccacttcact ttattacccg tcctgttttc aaaagtaatt tgccaccgaa actaagtaag      60
gatgacatag ttcattatgc acaccagtta cttgaaaaaa atacccataa tgaatagtga     120
tagtgatcta aaactccaaa aggtgtggat cgagcggcat gttgatcaag atgaacttag     180
tttaacaact actgcagttg aacttaaaaa gagtgatgaa caaaaacctg ttgccattaa     240
aagtagtgac tttattggtc atgaagagtt aatctctgtt ccagttttac taatcccaac     300
ccctgttgtt aaagagattg atcaaccagc agttattcct ccagttaaag caaaaccaaa     360
agcaactaaa aagaaaactc ctgttaaatc aaaaccaact agtaaatcaa ctaaacaaac     420
aaaacctaaa caatccaagc ccaaatcaaa acaagttcaa caaaccaaag ctaaaccaac     480
ccaaattcaa acaaaaaaaa gcaataaaaa aaccagatct taatctggtt tttttagtgt     540
taacaacagt agttttaact aaaaactgga aggaatagg aagaactacc tggggttaat     600
```

<210> SEQ ID NO 45
<211> LENGTH: 588
<212> TYPE: DNA
<213> ORGANISM: Artificial sequence
<220> FEATURE:
<223> OTHER INFORMATION: DNA sequence including Mg219 gene

<400> SEQUENCE: 45

```
actttattac ccgtcctgtt ttcaaaagta atttgccacc gaaactaagt aaggatgaca      60
tagttcatta tgcgcaccag ttacttgaaa aaaataccca taatgaatag tgatagtgat     120
ctaaaactcc aaaaggtgtg gatcgagcgg catgttgatc aagatgaact tagtttaaca     180
actactgcag ttgaacttaa aaagagtgat gaacaaaaac ctgttgccat taaaagtagt     240
gactttattg gtcatgaaga gttaatctct gttccagttt tactaatccc aacccctgtt     300
gttaaagaga ttgatcaacc agcagttatt cctccagtta agcaaaaacc aaaagcaact     360
aaaaagaaaa ctcctgttaa atcaaaacca actagtaaat caactaaaca acaaaacct     420
aaacaatcca agcccaaatc aaaacaagtt caacaaacca agctaaacc aacccaaatt     480
caaacaaaaa aaagcaataa aaaaaccaga tcttaatctg ttttttttag tgttaacaac     540
agtagtttta actaaaaact ggaaaggaat aggaagaact acctgggg                 588
```

<210> SEQ ID NO 46
<211> LENGTH: 593
<212> TYPE: DNA
<213> ORGANISM: Artificial sequence
<220> FEATURE:
<223> OTHER INFORMATION: DNA sequence including Mg219 gene

<400> SEQUENCE: 46

```
actttattac ccgtcctgtt ttcaaaagta atttgccacc gaaactaagt aaggatgaca      60
tagttcatta tgcgcaccag ttacttgaaa aaaataccca taatgaatag tgatagtgat     120
ctaaaactcc aaaaggtgtg gatcgagcgg catgttgatc aagatgaact tagtttaaca     180
actactgcag ttgaacttaa aaagagtgat gaacaaaaac ctgttgccat taaaagtagt     240
gactttattg gtcatgaaga gttaatctct gttccagttt tactaatccc aacccctgtt     300
```

```
gttaaagaga ttgatcaacc agcagttatt cctccagtta agcaaaaacc aaaagcaact      360
aaaaagaaaa ctcctgttaa atcaaaacca actagtaaat caactaaaca aacaaaacct      420
aaacaatcca agcccaaatc aaaacaagtt caacaaacca agctaaacc aacccaaatt       480 caaacaaaaa aaagcaataa aaaaaccaga tcttaatctg gttttttttag tgttaacaac    540 agtagtttta actaaaaact ggaaaggaat aggaagaact acctggggtt aat             593

<210> SEQ ID NO 47
<211> LENGTH: 626
<212> TYPE: DNA
<213> ORGANISM: Artificial sequence
<220> FEATURE:
<223> OTHER INFORMATION: DNA sequence including Mg219 gene

<400> SEQUENCE: 47
ccacttaact ttattacccg tcctgttttc aaaagtaatt tgccaccaaa actaagtaag      60
gatgacatag ttcattatgc gcaccagtta cttgaaaaaa atacccataa tgaatagtga     120
tagtgatcta aaactccaaa aggtgtggat cgagcggcat gttgatcaag atgaacttag     180
tttaacaact actgcagttg aacttaaaaa gagtgatgaa caaaaacctg ttgccattaa     240
aagtagtgac tttattggcc atgaagaatt aatctctgtt ccagttttac taatcccaac     300
ccctgttgtt aaagagattg accaaccagt agttattact ccagttaaag caaaaccaaa     360
agcaactaaa aagaaaactc ctgttaaatc aaaaccaact aataaatcaa ctaaacaaac     420
aaaacctaaa caacccaaac ccaaatcaaa acaagttcaa aaaccaaag ctaaaccaaa      480 agcaactaaa caaaccaaaa caaagccaac ccaaattcaa acaaaaaaaa gcaataaaaa     540
aaccagatct taatctggtt ttttttagtgt taacaacagt agttttaact aaaaactgga    600
aaggaatagg aagaactacc tggggt                                          626

<210> SEQ ID NO 48
<211> LENGTH: 625
<212> TYPE: DNA
<213> ORGANISM: Artificial sequence
<220> FEATURE:
<223> OTHER INFORMATION: DNA sequence including Mg219 gene

<400> SEQUENCE: 48
ttgaaaaaac aacagaagaa aaaaccactt aactttatta cccgtcctgt tttcaaaagt      60
aatttgccac cgaaactaag taaggatgac atagttcatt atgcgcacca gttacttgaa    120 aaaaatacccc ataatgaata gtgatagtga tctaaaactc caaaaggtgt ggatcgagcg    180
gcatgttgat caagatgaac ttagtttaac aactactgca gttgaactta aaaagagtga    240
tgaacaaaaa cctgttgcca ttaaaagtag tgactttatt ggtcatgaag agttaatctc    300
tgttccagtt ttactaatcc caacccctgt tgttaaagag attgatcaac cagcagttat    360
tcctccagtt aaagcaaaac caaagcaac taaaaagaaa actcctgtta atcaaaacc     420 aactagtaaa tcaactaaac aaacaaaacc taaacaatcc aagcccaaat caaacaagt    480 tcaacaaacc aaagctaaac caacccaaat tcaaacaaaa aaagcaata aaaaaaccag    540 atcttaatct ggtttttta gtgttaacaa cagtagtttt aactaaaaac tggaaggaa      600 taggaagaac tacctggggt taatc                                           625
```

MYCOPLASMA GENITALIUM DETECTION ASSAY BASED ON THE MG219 GENE

The present invention relates to detection of *Mycoplasma* sp., in particular, *Mycoplasma genitalium*, and to reagents and kits therefor.

The Class Mollicutes contains Gram-positive bacteria that lack a cell wall, including the genera *Mycoplasma, Acholeplasma* and *Ureaplasma*. There are over 100 species of *Mycoplasma* alone, and 17 species of Mollicutes are considered a part of the human flora—including *M. pneumoniae, M. genitalium, M. fermentans* and *M. penetrans*.

Human and mammalian *Mycoplasmas* infect cells comprising mucus membranes and can have strict host and tissue specificities. By way of example, the primary tissue infected by *M. pneumoniae* is the respiratory tract, whereas *M. genitalium* primarily infects the urogenital tract.

*M. genitalium* is sexually transmissible, with a transmission rate that is believed to be similar to *Chlamydia trachomatis*. Indeed, clinicians working in the field have described *M. genitalium* as "the next *Chlamydia*". *M. genitalium* is a causative agent in urogenital tract diseases, in particular non-gonococcal urethritis (NGU). *M. genitalium* has also been implicated in pelvic inflammatory disease (PID) and infertility in women. Extragenital infections with *M. genitalium* may also occur, for example in the respiratory tract, in the eye, and in synovial fluid—leading to sexually acquired reactive arthritis (SARA).

Antibiotics used for the treatment of mycoplasmal infections belong to tetracyclines, macrolides-lincosamides and fluoroquinolones. These products are highly active in vitro against *Mycoplasmas*. However, some of these antibiotics have a differential activity according to species, and acquired resistance has been reported, mainly in genital *Mycoplasmas*. By way of example, *M. genitalium* is resistant to chloramphenicol. Most mycoplasmal infections are treated using adapted antibiotics, but they may be difficult to treat in immunosuppressed patients.

*Mycoplasmas* such as *M. genitalium* are very difficult to study by classical genetic methods, both because of their fastidious growth requirements and as a consequence of the absence of selectable markers. As a consequence, isolates have been very difficult to obtain.

Furthermore, the antigenic relationship between *M. pneumoniae* and *M. genitalium* leads to cross-reactions, which significantly hamper the use of serology for diagnostic and epidemiological studies.

Hybridization based techniques for detection of *Mycoplasmas* include the use of DNA probes. By way of example, radiolabelled oligonucleotide probes have been described that target the *M. genitalium* 16S rRNA.

Because of the problems encountered using traditional procedures for the diagnosis of *M. genitalium* infection, such as culture and serology, knowledge about its pathogenicity has been slow to accrue. Extensive clinical studies have only become possible with the advent of PCR-based assays.

PCR has proven a particularly useful tool for detecting fastidious *Mycoplasmas* due to its very high sensitivity (Jensen, Dan. Med. Bull. 2006; 53: 1-27). However, until recently, a major drawback of this technique has been the lack of commercial kits.

PCR assays have recently been developed that amplify and detect the *M. genitalium* MgPa gene (e.g. Jensen et al., J. Clinical Microbiology, February 2004, pages 683-692). The MgPa gene encodes the major *M. genitalium* adhesion protein responsible for attachment to host cells, in particular for attachment to the epithelial cells, such as those of the human fallopian tube.

Evasion of the host immune system by antigenic variation of surface components such as adhesins enables *Mycoplasma* such as *M. genitalium* to adapt to changing environments and selection pressures. This antigenic variation leads to considerable sequence variation in genes that encode surface proteins such as the MgPa gene. Thus, diagnostic assays that rely on detection of surface proteins and corresponding nucleic acids fail to detect some variants, resulting in poor sensitivity of the assay.

Other published PCR-based assays for detecting *M. genitalium* are directed towards the 16S rRNA gene (Yoshida et al., J. Clin. Microbiol. 2002: 40:1451-1455). However, the specificity and sensitivity of this assay has been put into question due to the high level of homology between the *M. pneumoniae* and *M. genitalium* 16S rRNA genes, and the preponderance of secondary structures in the 16SrRNA.

A LightCycler assay has also been described, directed towards detection of the P115 (MG299) gene with locked nucleic acid probes (Dupin et al., Clin. Infect. Dis. 2003; 37:602-605).

There is, therefore, a need to provide an alternative and/or improved system for detecting *M. genitalium*.

According to a first aspect, the present invention provides a method for detecting *M. genitalium* nucleic acid in a sample, comprising: (i) amplifying a nucleic acid sequence comprising SEQ ID NO: 1 or a fragment thereof; and (ii) detecting said amplified nucleic acid sequence.

According to a second aspect, the present invention provides a method for detecting *M. genitalium* nucleic acid in a sample, comprising: (i) contacting said sample with a probe, wherein the probe binds to a target sequence within SEQ ID NO: 1, or the complement thereof; and (ii) detecting binding of said probe to said target site.

The present invention provides improved specificity and sensitivity compared to existing PCR-based tests for *M. genitalium*.

The *M. genitalium* Mg219 gene (SEQ ID NO: 1) is 447 nucleotides long and encodes a 148 amino acid polypeptide of unknown function (SEQ ID NO: 2).

The Mg219 gene (SEQ ID NO: 1) is located from nucleotide residue 265596 to nucleotide residue 266042 of the complete genome of *M. genitalium* (as detailed in Accession No. NC_000908, *M. genitalium* G-37).

Mg219 is found within an operon consisting of the Mg217, Mg218 and Mg219 genes, and transcription of Mg219 is continuous from Mg217 and Mg218 (Musatovova O. et al., FEMS Microbiol. Lett., 2003, 5, 229(1) pages 73-81). Mg218 encodes a high molecular mass cytadherence-related protein required for tip-mediated adherence. The function of Mg219 remains unknown, but due to the proximity to Mg218 in the *M. genitalium* genome, it is possible that Mg219 may be involved in adherence.

A detailed review by the present Applicant of all published *Mycoplasma* whole genome sequences revealed that the Mg219 gene has no homologues in *Mycoplasma* species other than *M. genitalium*.

Furthermore, by searching published genetic and protein databases, the present Applicant was unable to identify any gene having significant homology to the Mg219 gene, or any protein having significant homology to the encoded Mg219 polypeptide.

These findings were confirmed using the ORFANGE web-based program, which identifies genes that are only found once in a bacterial genome and not in other genomes.

Thus, the present Applicant has unexpectedly identified that the Mg219 gene is specific to *M. genitalium*, and is thus useful for identification of *M. genitalium* in a sample.

It is particularly important to keep the incidence of "false positive" results as low as possible in the field of detecting and diagnosing sexually transmitted diseases, due to the sensitive nature of the test results for the patient, cost and implications of inappropriate treatment, and the legal implications of providing an incorrect result.

Advantageously, because the Mg219 gene has no sequence homologues in other *Mycoplasma* species, or in other published sequence databases, the detection assay of the present invention, which is based on detection of Mg219 nucleic acid sequences, is very specific, with a very low incidence of "false positive" results.

As illustrated in the Examples (below), when a detection assay according to one embodiment of the present invention was tested by the present Applicant against DNA from all known human Mollicutes, some other bacterial species and pathogenic micro-organisms, the assay only detected *M. genitalium* thus illustrating the high degree of specificity of the assay.

The target Mg219 gene detected in the present invention is also an advantageous target gene because it is conserved between different strains of *M. genitalium*. Thus, the assay of the present invention advantageously detects all known strains of *M. genitalium* that have been tested in the assay to date.

A sample may be for instance, a food, sewerage, environmental, veterinary or clinical sample. In one aspect, the method may be used for detection of *M. genitalium* in a clinical sample.

Clinical samples may include urethral swabs, vaginal swabs, cervical swabs, rectal swabs, penile swabs, throat/oral swabs, urine, blood, respiratory tract samples, synovial fluids, cerebro-spinal fluid, liquid based cytology samples, tissue biopsies, ulcer samples, conjunctivitis samples and any other samples from animals, particularly from humans. In one aspect, the sample may comprise semen or eggs.

Thus, in one aspect, the method of the present invention comprises the step of amplifying *M. genitalium* nucleic acid.

In this application, the expressions "amplified nucleic acid sequence" and "amplicon" are used interchangeably and have the same meaning.

Specifically, in one aspect, the method of the present invention comprises amplifying a nucleic acid sequence comprising SEQ ID NO: 1. The amplified nucleic acid sequence (amplicon) may consist of SEQ ID NO: 1.

In one aspect, the method of the present invention comprises amplifying a nucleic acid sequence comprising a fragment of SEQ ID NO: 1. The amplified nucleic acid sequence (amplicon) may consist of a fragment of SEQ ID NO: 1.

Alternatively, the amplicon may comprise a fragment of SEQ ID NO: 1 and also 1 or more additional nucleotides that are located upstream or downstream of SEQ ID NO: 1 in the *M. genitalium* genome.

A fragment of SEQ ID NO: 1 is preferably at least 10 consecutive nucleotides of SEQ ID NO: 1, and is more preferably at least 25 nucleotides, more preferably at least 50 nucleotides, and may be at least 75, 100, 125, 150, 175, 200, 225, 250, 275, 300, 325, 350, 375 or 400 nucleotides of SEQ ID NO: 1. A fragment of SEQ ID NO: 1 is preferably up to 440 consecutive nucleotides of SEQ ID NO: 1, more preferably up to 425 nucleotides, more preferably up to 400 nucleotides, and may be up to 375, 350, 325, 300, 275, 250, 225, 200, 175, 150, 125, 100, 75, 50, or 25 nucleotides of SEQ ID NO: 1.

In a specific example, the amplicon may comprise a stretch of consecutive nucleotides spanning the nucleotide located 11 positions upstream of SEQ ID NO: 1 in the *M. genitalium* genome (i.e. nucleotide position −11) to the nucleotide at position 240 of SEQ ID NO: 1. Thus, in this specific example, the amplicon comprises a 240 nucleotide fragment of SEQ ID NO: 1, from nucleotide 1 of SEQ ID NO: 1 to nucleotide 240 of SEQ ID NO: 1 (plus the 11 nucleotides upstream of SEQ ID NO: 1 in the *M. genitalium* genome).

Amplification may be carried out by methods known in the art, preferably by PCR. Examples of PCR platforms suitable for conducting the amplification step of the present invention include real-time platforms such as Rotor-gene, LightCycler and Taqman platforms.

In one aspect, amplification of *M. genitalium* nucleic acid is carried out using a pair of sequence specific oligonucleotide primers, wherein said primers bind to target sites in the *M. genitalium* nucleic acid. Under suitable conditions, the primers are extended, resulting in nucleic acid synthesis. A skilled person would be able to determine suitable conditions for promoting amplification of a nucleic acid sequence comprising a fragment of SEQ ID NO: 1.

For the avoidance of doubt, in the context of the present invention, the definition of an oligonucleotide primer does not include the full length Mg219 gene (or complement thereof).

Primers of the present invention are designed to bind to the target gene sequence based on the selection of desired parameters, using conventional software, such as Primer Express (Applied Biosystems). In this regard, it is preferred that the binding conditions are such that a high level of specificity is provided. The melting temperature (Tm) of the primers is preferably in excess of 50° C. and is most preferably about 60° C. A primer of the present invention preferably binds to target *M. genitalium* nucleic acid but is preferably screened to minimise self-complementarity and dimer formation (primer-to-primer binding).

The primer pair comprises forward and reverse oligonucleotide primers.

A forward primer binds to the complementary (i.e. antisense) strand of the target *M. genitalium* nucleic acid and a reverse primer binds to the coding (sense) strand of the target *M. genitalium* nucleic acid.

The forward and reverse oligonucleotide primers are typically at least 5 nucleotides long, preferably at least 10 nucleotides long, more preferably at least 15, 20, 25, 30, 35, 40, 45 or 50 nucleotides long. Preferably, the primers are up to 60 nucleotides long, preferably up to 55 nucleotides long, more preferably up to 50, 45, 40, 35, 30, 25, 20, 15 or 10 nucleotides long.

In one aspect, the forward primer and/or the reverse primer is about 50-55 nucleotides long. In one aspect, the forward primer and/or the reverse primer is about 20-25 nucleotides long. In one aspect, the forward primer and/or the reverse primer is about 25-30 nucleotides long. In one aspect, the forward primer is about 29 nucleotides long and the reverse primer is about 27 nucleotides long. It is an advantage to use shorter primers, as this enables faster annealing to target nucleic acid.

The forward primer binds to a target site within the *M. genitalium* nucleic acid. This target site may be located within the complement of SEQ ID NO: 1—i.e. the target site may be located between nucleotide 1 and nucleotide 447 of the complement of SEQ ID NO: 1.

Reference to "a target site between (for example) nucleotide residues 1 and 447 of the complement of SEQ ID NO: 1" does not imply that the target site extends between or is defined by the recited residues. Thus, the target site for the forward primer may be 447 nucleotides long, or may be shorter, even considerably shorter than 447 nucleotides in length (e.g. up to about 200, 100, 75, 60, 50, 40, 30, 25, 20, 15, 10 nucleotides long), so long as it is located somewhere within the recited range of nucleotide residues.

In one aspect, the target site of the forward primer is about 50-55 nucleotides long. In one aspect, the target site of the forward primer is about 25-30 nucleotides long, preferably about 29 nucleotides long.

Alternatively, the target site for the forward primer within the *M. genitalium* nucleic acid may be located within upstream nucleic acid sequences that flank the complement of SEQ ID NO: 1 in the *M. genitalium* genome.

SEQ ID NO: 1 is located from nucleotide residue 265596 to nucleotide residue 266042 of the complete genome of *M. genitalium* (as detailed in Accession No. NC_000908, *M. genitalium* G-37). Thus, the nucleic acid sequences that are located upstream of the complement of SEQ ID NO: 1 in the *M. genitalium* genome have nucleotide numbers 1-265595.

Alternatively, the forward primer may bind to a target site that overlaps the complement of SEQ ID NO: 1 and upstream nucleic acid sequences that flank the complement of SEQ ID NO: 1 in the *M. genitalium* genome.

Upstream nucleotides are typically designated using negative numbers. By way of example, the nucleotide residue 11 residues upstream from the start of the complement of SEQ ID NO: 1 in the *M. genitalium* genome (i.e. nucleotide residue 265585 of the complete *M. genitalium* genome) is designated "nucleotide −11".

The nucleic acid sequence of the 60 nucleotide residues located upstream from SEQ ID NO: 1 in the *M. genitalium* genome (i.e. nucleotides −60 to −1 of SEQ ID NO: 1) are represented by SEQ ID NO: 6. Thus, nucleotide residue number 1 of SEQ ID NO: 6 is nucleotide residue number −60 of SEQ ID NO: 1, and nucleotide residue number 60 of SEQ ID NO: 6 is nucleotide residue number −1 of SEQ ID NO: 1.

In one aspect, the forward primer binds to a target site located between nucleotides −80 to +450 of a nucleic acid strand complementary to SEQ ID NO: 1. Within this range of nucleotide residues, the target site for the forward primer is preferably located from nucleotide residue −76 of a nucleic acid strand complementary to SEQ ID NO: 1, and may be located from nucleotide residue −60, −55, −53, −50, −25, −10, 1, 25, 51, 101, 151, 201, 251, 301, 351 or 401 of a nucleic acid strand complementary to SEQ ID NO: 1. Preferably, the target site for the forward primer is located up to nucleotide residue 447 of a nucleic acid strand complementary to SEQ ID NO: 1, and may be located up to nucleotide residue 425, 400, 350, 300, 250, 200, 150, 100, 50, 25, 1, −5, −10, −25, −50 or −55 of a nucleic acid strand complementary to SEQ ID NO: 1.

In one aspect, the forward primer binds to a target site located between nucleotide residues −25 to 25 of a nucleic acid strand complementary to SEQ ID NO: 1. Preferably, the target site for the forward primer is located from nucleotide residue −20, −15, −14, −13 or −12 and up to nucleotide residue 22, or 19 of a nucleic acid strand complementary to SEQ ID NO: 1.

In one aspect, the target site for the forward primer is defined by nucleotide residues −11 to 18 of a nucleic acid strand complementary to SEQ ID NO: 1. This target region consists of nucleotide residues 50-60 of a nucleic acid strand complementary to SEQ ID NO: 6, followed by nucleotide residues 1-18 of a nucleic acid strand complementary to SEQ ID NO: 1.

For the avoidance of any doubt, the above numbering system applied to the nucleic acid residues of the complementary strand of SEQ ID NO: 1 (and upstream sequences, SEQ ID NO: 6) is based on the numbering of the nucleic acids of SEQ ID NO: 1 (and upstream sequences, SEQ ID NO: 6) to which they are complementary.

The reverse primer binds to a target site within the *M. genitalium* nucleic acid. This target site may be located within SEQ ID NO: 1—i.e. the target site may be located between nucleotide 1 and nucleotide 447 of SEQ ID NO: 1.

Reference to "a target site between (for example) nucleotide residues 1 and 447 of SEQ ID NO: 1" does not imply that the target site extends between or is defined by the recited residues. Thus, the target site for the reverse primer may be 447 nucleotides long, or may be shorter, even considerably shorter than 447 nucleotides in length (e.g. up to 200, 100, 75, 60, 50, 40, 30, 25, 20, nucleotides long), so long as it is located somewhere within the recited range of nucleotide residues.

In one aspect, the target site for the reverse primer is about 50-55 nucleotides long. In one aspect, the target site for the reverse primer is about 25-30 nucleotides long, preferably about 27 nucleotides long.

Alternatively, the target site for the reverse primer within the *M. genitalium* nucleic acid may be located within downstream nucleic acid sequences that flank SEQ ID NO: 1 in the *M. genitalium* genome.

SEQ ID NO: 1 is located from nucleotide residue 265596 to nucleotide residue 266042 of the complete genome of *M. genitalium* (as detailed in Accession No. NC__000908, *M. genitalium* G-37). Thus, the nucleic acid sequences that are located downstream of SEQ ID NO: 1 in the *M. genitalium* genome have nucleotide numbers 266043 to 580074.

Alternatively, the reverse primer may bind to a target site that overlaps SEQ ID NO: 1 and downstream nucleic acid sequences that flank SEQ ID NO: 1 in the *M. genitalium* genome.

Downstream nucleotides are designated with positive numbers, continuing from the number of the last nucleotide of SEQ ID NO: 1 (residue 447). By way of example, the nucleotide residue located 20 residues downstream from the end of SEQ ID NO: 1 in the *M. genitalium* genome (i.e. nucleotide residue 266063 of the complete *M. genitalium* genome) is designated "nucleotide +467" (i.e. 447+20=467).

The nucleic acid sequence of the 53 nucleotide residues located downstream from SEQ ID NO: 1 in the *M. genitalium* genome (i.e. nucleotides +448 to +500 of SEQ ID NO: 1) are represented by SEQ ID NO: 7. Thus, nucleotide residue number 1 of SEQ ID NO: 7 is nucleotide residue number +448 of SEQ ID NO: 1, and nucleotide residue number 53 of SEQ ID NO: 7 is nucleotide residue number +500 of SEQ ID NO: 1.

In one aspect of the invention, the reverse primer binds to a target site between nucleotide residues −5 to +525 of SEQ ID NO: 1. Within this range of nucleotide residues, the target site for the reverse primer is preferably located from nucleotide residue −3 of SEQ ID NO: 1, and may be located from nucleotide residue 1, 10, 25, 48, 98, 148, 198, 248, 298, 348, 398, +448 or +503 of SEQ ID NO: 1. Preferably, within this range of nucleotide residues, the target site for the reverse primer is located up to nucleotide residue +502 of SEQ ID NO: 1, and may be located up to nucleotide residue 447, 397, 347, 297, 247, 197, 147, 97, 47 or 25 of SEQ ID NO: 1.

In one aspect, the reverse primer binds a target site between nucleotide residues 200 to 250 of SEQ ID NO: 1. Within the range of nucleotide residues, the target site for the reverse primer is preferably located from nucleotide residue 205, 210, 211, 212 or 213 of SEQ ID NO: 1 and up to nucleotide residue 245, 244, 243, 242 or 241 of SEQ ID NO: 1. In one aspect, the reverse primer binds to a target region defined by residues 214 to 240 of SEQ ID NO: 1.

The amplified nucleic acid sequence (amplicon) is preferably at least 10 nucleotides long, more preferably at least 20 nucleotides long, more preferably at least 40 nucleotides long, and may be at least 50, 75, 100, 125, 150, 175, 200, 225, 250, 275, 300, 325, 350, 375 or 400 nucleotides long. The amplicon is preferably up to 440 nucleotides long, preferably up to 425 nucleotides long, more preferably up to 400 nucleotides long, and may be up to 375, 350, 325, 300, 275, 250, 225, 200, 175, 150, 125, 100, 75, 50, 40 or 20 nucleotides long. In one aspect, the amplicon is about 225-275 nucleotides long, preferably about 251 nucleotides long.

Particularly good results have been obtained using a forward primer selected from SEQ ID NOs: 4, 8 or 31, as shown in the table below, which bind to a target site defined by nucleotide residues −11 to 18 of a nucleic acid strand complementary to SEQ ID NO: 1.

| SEQ ID NO: | SEQUENCE |
|---|---|
| 4 | 5' GAC AGT TCA TTA TGC GCA CCA GTT ACT TG 3' |
| 8 | 5' CAT AGT TCA TTA TGC GCA CCA GTT ACT TG 3' |
| 31 | 5' CAT AGT TCA TTA TGC ACA CCA GTT ACT TG 3' |

Particularly good results have been obtained using a forward primer selected from SEQ ID NOs: 9-19, as shown in the table below (see also Example 4).

9 5' CCA CTT AAC TTT ATT ACC CGT CC 3'

10 5' TGT TTT CAA AAG TAA TTT GCC ACC GAA ACT AAG TAA GGA TGA CAT AGT TCA TT 3'

11 5' ATG CGC ACC AGT TAC TTG AAA AAA ATA CCC ATA ATG AAT AGT GAT AGT GA 3'

12 5' TCT AAA ACT CCA AAA GGT GTG GAT CGA GCG GCA TGT TGA TCA AGA TGA AC 3'

13 5' TTA GTT TAA CAA CTA CTG CAG TTG AAC TTA AAA AGA GTG ATG AAC AAA AA 3'

14 5' CCT GTT GCC ATT AAA AGT AGT GAC TTT ATT GGT CAT GAA GAG TTA ATC TC 3'

15 5' TGT TCC AGT TTT ACT AAT CCC AAC CCC TGT TGT TAA AGA GAT TGA TCA AC 3'

16 5' CAG CAG TTA TTC CTC CAG TTA AAG CAA AAC CAA AAG CAA CTA AAA AGA AA 3'

17 5' ACT CCT GTT AAA TCA AAA CCA ACT AGT AAA TCA ACT AAA CAA ACA AAA CC 3'

18 5' TAA ACA ATC AAA GCC AAA ATC AAA ACA AGT TCA ACA AAC CAA AGC TAA AC 3'

19 5' CAA CCC AAA TTC AAA CAA AAA AAA GCA ATA AAA AAA CCA GAT CTT AAT CT 3'

Particularly good results have been obtained using a reverse primer of SEQ ID NO: 5, as shown in the table below, which binds to a target site defined by nucleotide residues 214 to 240 of SEQ ID NO: 1.

| SEQ ID NO: | SEQUENCE |
|---|---|
| 5 | 5' CTC TTT AAC AAC AGG GGT TGG GAT TAG 3' |

Particularly good results have been obtained using a reverse primer selected from SEQ ID NOs: 20-30, as shown in the table below (see also Example 4).

20 5' GAT TAA CCC CAG GTA GTT CTT CC 3'

21 5' TAT CCC TTT CCA GTT TTT AGT TAA AAC TAC TGT TGT TAA CAC TAA AAA AAC CAG A3'

22 5' TTA AGA TCT GGT TTT TTT ATT GCT TTT TTT TGT TTG AAT TTG GGT TGG TT 3'

23 5' TAG CTT TGG TTT GTT GAA CTT GTT TTG ATT TGG GCT TGG ATT GTT TAG GT 3'

24 5' TTT GTT TGT TTA GTT GAT TTA CTA GTT GGT TTT GAT TTA ACA GGA GTT TT 3'

25 5' CTT TTT AGT TGC TTT TGG TTT TGC TTT AAC TGG AGG AAT AAC TGC TGG TT 3'

26 5' GAT CAA TCT CTT TAA CAA CAG GGG TTG GGA TTA GTA AAA CTG GAA CAG AG 3'

27 5' ATT AAC TCT TGA TGA CCA ATA AAG TCA CTA CTT TTA ATG GCA ACA GGT TT 3'

28 5' TTG TTC ATC ACT CTT TTT AAG TTC AAC TGC AGT AGT TGT TAA ACT AAG TT 3'

29 5' CAT CTT GAT CAA CAT GCC GCT CGA TCC ACA CCT TTT GGA GTT TTA GAT CA 3'

30 5' CTA TCA CTA TTC ATT ATG GGT ATT TTT TTC AAG TAA CTG GTG CGC ATA AT 3'

It will, however, be appreciated that variants may be employed, which differ from the above-mentioned primer sequences by one or more nucleotides. In this regard, conservative substitutions are preferred.

Thus, in one aspect, the forward primer comprises a nucleic acid sequence having at least 60%, preferably at least 65%, preferably at least 70%, preferably at least 75%, preferably at least 80%, preferably at least 85%, preferably at least 90%, preferably at least 95%, more preferably at least 97%, most preferably 100% sequence identity to a sequence selected from SEQ ID NOs: 4, 8-19 or 31.

Thus, in one aspect, the reverse primer comprises a nucleic acid sequence having at least 60%, preferably at least 65%, preferably at least 70%, preferably at least 75%, preferably at least 80%, preferably at least 85%, preferably at least 90%, preferably at least 95%, more preferably at least 97%, most preferably 100% sequence identity to a sequence selected from SEQ ID NO: 5 or SEQ ID NOs: 20-30.

Preferably, the forward primer consists of a nucleic acid sequence having at least 60%, preferably at least 65%, preferably at least 70%, preferably at least 75%, preferably at least 80%, preferably at least 85%, preferably at least 90%, preferably at least 95%, more preferably at least 97%, most preferably 100% sequence identity to a sequence selected from SEQ ID NO: 4, 8-19 or 31.

Preferably, the reverse primer consists of a nucleic acid sequence having at least 60%, preferably at least 65%, preferably at least 70%, preferably at least 75%, preferably at least 80%, preferably at least 85%, preferably at least 90%, preferably at least 95%, more preferably at least 97%, most preferably 100% sequence identity to a sequence selected from SEQ. ID NOs: 5 or 20-30.

Fragments of the above-mentioned primer sequences may also be employed.

Preferably, a fragment of forward primers SEQ ID NOs: 4, 8 and 31 comprises at least 15 consecutive nucleotides of said primer sequences, more preferably at least 20, 21, 22, 23, 24, 25, 26 or 27 consecutive nucleotides of said primer sequences, and may comprise up to 28 consecutive nucleotides of said primer sequences.

Preferably, a fragment of reverse primer SEQ ID NO: 5 comprises at least 15 consecutive nucleotides of said primer sequence, more preferably at least 20, 21, 22, 23, 24 or 25 consecutive nucleotides of said primer sequence, and may comprise up to 26 consecutive nucleotides of said primer sequence.

Preferably, a fragment of primer SEQ ID NOs: 9 and 20 comprises at least 10 consecutive nucleotides of said primer sequences, more preferably at least 15, 16, 17, 18, 19, 20 or 21 consecutive nucleotides of said primer sequences, and may comprise up to 22 consecutive nucleotides of said primer sequences.

Preferably, a fragment of primer SEQ ID NOs: 10-30 comprises at least 30 consecutive nucleotides of said primer sequences, more preferably at least 35, 40, 41, 42, 43, 44, 45, 46, 47 or 48 consecutive nucleotides of said primer sequences, and may comprise up to 49 consecutive nucleotides of said primer sequences.

In the method of the present invention, any forward primer selected from SEQ ID NOs: 4, 8-19 or 31 (or fragments thereof, or variants thereof having a % identity thereto as discussed above) may be used in combination with any reverse primer selected from SEQ ID NOs: 5 or 20-30 (or fragments thereof, or variants thereof having a % identity thereto as discussed above).

In one aspect, the method may employ forward primer SEQ ID NO: 4, 8 or 31 and reverse primer SEQ ID NO: 5 (or fragments thereof, or variants thereof having % identity thereto as discussed above).

In one aspect, the method may employ forward primer SEQ ID NO: 9 and reverse primer SEQ ID NO: 20 (or fragments thereof, or variants thereof having % identity thereto as discussed above).

It is an option for at least one of the primers to comprise a minor groove binder (MGB) component.

The detection step may be carried out by any known means. In one aspect, the amplified nucleic acid sequence is detected by a method comprising gel electrophoresis.

Alternatively, or in addition, the step of detecting the amplified nucleic acid sequence may comprise contacting said amplified nucleic acid sequence with a probe, wherein the probe binds to a target site within said amplified nucleic acid sequence, or the complement thereof, and detecting binding of said probe to said amplified nucleic acid sequence.

Suitable probes for use in the methods of the present invention are ligands that bind specifically to *M. genitalium* nucleic acid. Such ligands may be oligonucleotide ligands or protein ligands, for example, antibodies. However, it is preferred that the probes are oligonucleotide probes.

For the avoidance of doubt, in the context of the present invention, the definition of an oligonucleotide probe does not include the full length Mg219 gene (or complement thereof).

Probes are designed to bind to the target gene sequence (i.e. within the amplicon, or within SEQ ID NO: 1) based on a selection of desired parameters, using conventional software. It is preferred that the binding conditions are such that a high level of specificity is provided—i.e. binding occurs under "stringent conditions". In general, stringent conditions are selected to be about 5° C. lower than the thermal melting point ($T_m$) for the specific sequence at a defined ionic strength and pH. The $T_m$ is the temperature (under defined ionic strength and pH) at which 50% of the target sequence binds to a perfectly matched probe. In this regard, the $T_m$ of probes of the present invention, at a salt concentration of about 0.02 M or less at pH 7, is preferably above 60° C., more preferably about 70° C. Premixed binding solutions are available (e.g. EXPRESSHYB Hybridisation Solution from CLONTECH Laboratories, Inc.), and binding can be performed according to the manufacturer's instructions. Alternatively, a person skilled in the art can devise variations of these binding conditions.

Following binding, washing under stringent (preferably highly stringent) conditions removes unbound nucleic acid molecules. Typical stringent washing conditions include washing in a solution of 0.5-2×SSC with 0.1% SDS at 55-65° C. Typical highly stringent washing conditions include washing in a solution of 0.1-0.2×SSC with 0.1% SDS at 55-65° C. A skilled person can readily devise equivalent conditions for example, by substituting SSPE for the SSC in the wash solution.

It is preferable to screen the probes to minimise self-complementarity and dimer formation (probe-probe binding). Preferred probes of the present invention are selected so as to have minimal homology with human DNA. The selection process may involve comparing a candidate probe sequence with human DNA and rejecting the probe if the homology is greater than 50%. The aim of this selection process is to reduce annealing of probe to contaminating human DNA sequences and hence allow improved specificity of the assay.

In one embodiment, conjugation of a minor groove binder (MGB) to the probe stabilises nucleic acid duplexes, causing a desirable increase in oligonucleotide Tm (the temperature at which the duplex separates). This increase in Tm enables considerably shorter probes to be used than would otherwise be possible.

In one aspect, the oligonucleotide probe is at least 5 nucleotides long, more preferably at least 10 nucleotides long, more preferably at least 12, 13, 14, 15 or 16 nucleotides long. Preferably, the probe is up to 50 nucleotides long, more preferably up to 30 nucleotides long, and more preferably up to 20, 19 or 18 nucleotides long. It is an advantage to use shorter probes, as this enables faster annealing to target *M. genitalium* nucleic acid.

The complement of a nucleic acid sequence binds via complementary base-pairing to the nucleic acid sequence. In the present invention, a "complementary strand" means the anti-sense nucleic acid strand, which binds via complementary base-pairing to a sense strand.

Thus, in one aspect, the probe binds to a target sequence within the coding (sense) strand of the target *M. genitalium* nucleic acid (i.e. within SEQ ID NO: 1). In an alternative aspect, the probe binds to a target sequence within the complementary, non-coding (anti-sense) strand of the target *M. genitalium* nucleic acid (i.e. within the complement of SEQ ID NO: 1).

The target site to which the probe binds may be located anywhere within SEQ ID NO: 1, or within the complement of SEQ ID NO: 1. If the nucleic acid in the sample has previously been amplified, the probe binds to a target site within said amplified nucleic acid sequence, or the complement thereof.

Thus, in one aspect, the probe binds to a target site located anywhere between residues 1 and 447 of SEQ ID NO: 1, or the complement thereof. In this regard, reference to "a target site between (for example) residues 1 and 447 of SEQ ID NO: 1 or the complement thereof" does not imply that the target site extends between or is defined by the recited residues. Thus, the target site may be 447 nucleotides long, or may be shorter, even considerably shorter than 447 nucleotides in length (e.g. up to 200, 100, 75, 60, 50, 40, 30, 25, 20, 15 or 10 nucleotides long).

Thus, in one aspect, the probe binds to a target site between nucleic acid residues 1-447 of SEQ ID NO: 1 or the complement thereof. Within this range of nucleotide residues, the target site for the probe is preferably located from nucleotide residue 10 of SEQ ID NO: 1 or the complement thereof, more preferably from nucleotide residue 15 of SEQ ID NO: 1 or the complement thereof, and may be located from nucleotide residue 25, 50, 75, 100, 150, 200, 250, 300, 350 or 400 of SEQ ID NO: 1 or the complement thereof. Within this range of nucleotide residues, the target site for the probe is preferably located up to nucleotide residue 440, more preferably up to nucleotide residue 420 of SEQ ID NO: 1 or the complement thereof, and may be located up to residue 400, 350, 300, 250, 200, 150, 100 or 50 of SEQ ID NO: 1 or the complement thereof.

In one aspect, the probe binds to a target region located between nucleotide residues 50-100 of the nucleic acid strand complementary to SEQ ID NO: 1. Preferably, the target site for the probe is located from nucleotide residue 55, 60, 63, 64 or 65 and up to nucleotide residue 90, 85, 84 or 83 of the nucleic acid strand complementary to SEQ ID NO: 1. Most preferably, the target site for the probe is defined by residues 66-82 of the nucleic acid strand complementary to SEQ ID NO: 1.

For the avoidance of any doubt, the above numbering system applied to the nucleic acid residues of the complementary strand of SEQ ID NO: 1 is based on the numbering of the nucleic acids of SEQ ID NO: 1 to which they are complementary.

Good results have been obtained using a probe consisting of the nucleic acid sequence SEQ ID NO: 3, as shown in the table below.

| SEQ ID NO: | SEQUENCE |
|---|---|
| 3 | 5'-GGT GTG GAT CGA GCG GC-3' |

It will, however, be appreciated that variants may be employed, which differ from the above-mentioned probe sequence by one or more nucleotides. In this regard, conservative substitutions are preferred.

Thus, in one aspect, the probe comprises a nucleic acid sequence having at least 60%, preferably at least 65%, preferably at least 70%, preferably at least 75%, preferably at least 80%, preferably at least 85%, preferably at least 90%, preferably at least 95%, most preferably 100% sequence identity to SEQ ID NO: 3.

In one aspect, the probe consists of a nucleic acid sequence having at least 60%, preferably at least 65%, preferably at least 70%, preferably at least 75%, preferably at least 80%, preferably at least 85%, preferably at least 90%, preferably at least 95%, most preferably 100% sequence identity to SEQ ID NO: 3.

An alternative means for defining variant probe sequences is by defining the number of nucleotides that differ between the variant sequence and the probe sequence of the present invention. In this regard, the present invention embraces probe sequences that differ from SEQ ID NO: 3 by no more than 6 nucleotides, preferably by no more than 5 nucleotides, preferably by no more than 4 nucleotides, more preferably by no more than 3 nucleotides, yet more preferably by no more than 2 nucleotides, and most preferably by no more than 1 nucleotide.

A fragment of the above-mentioned probe sequence may also be employed, wherein the fragment comprises at least 10, preferably at least 11, 12, 13, 14, or 16 consecutive nucleotides of SEQ ID NO: 3.

In one aspect, the probe may be immobilised onto a solid support or platform. The support may be a rigid solid support made from, for example, glass or plastic, or else the support may be a nylon or nitrocellulose membrane, or other membrane. 3D matrices are suitable supports for use with the present invention—e.g. polyacrylamide or PEG gels. In one embodiment, the solid support may be in the form of beads, which may be sorted by size or fluorophores.

The probes may be immobilised to the solid support by a variety of means. By way of example, probes may be immobilised onto a nylon membrane by UV cross-linking. Biotin-labelled probes may be bound to streptavidin-coated substrates, and probes prepared with amino linkers may be immobilised onto silanised surfaces.

Another means of immobilising probe is via a poly-T tail, preferably at the 3' end. The poly-T tail consists of a run of from 1 to 100 thymine residues added to the probe at the 3' end with a terminal transferase. Preferably, from 1 to 20 thymine residues are added. The poly-T tail is then baked or UV cross-linked onto the solid substrate. Addition of a poly-T tail appears to have two functions. First, the poly-T tail increases the amount of probe that is immobilised onto the solid support. Second, the poly-T tail conforms the probe in such a way as to improve the efficiency of hybridisation.

It is an option for the probe to comprise a minor groove binder (MGB) component.

In one aspect, binding of probe to *M. genitalium* nucleic acid provides a detectable signal, which may be detected by known means. A detectable signal may be, for example, a radioactive signal or a fluorescent signal, such as a change in fluorescence.

In one embodiment, the probe is labelled and the assay comprises detecting the label and correlating presence of label with presence of *M. genitalium* nucleic acid. The label may be a radiolabel but is preferably non-radioactive, such as a fluorescent label. By way of example, the label may be digoxygenin or fluorescein-isothiocyanate (FITC).

The label may be detected directly, such as by exposure to photographic or X-ray film, or indirectly, for example, in a two-phase system. An example of indirect label detection is binding of an antibody to the label. In another aspect, the probe is labelled with biotin and is detected using streptavidin bound to a detectable molecule or to an enzyme, which generates a detectable signal.

In one aspect, prior to detecting binding of the probe to its target sequence, the method comprises amplifying *M. genitalium* nucleic acid. It may be desirable to amplify the target human papillomavirus nucleic acid if the sample is small and/or comprises a heterogeneous collection of DNA sequences.

Most preferably, the amplification step is carried out prior to contacting the nucleic acid with the probe.

Amplification of *M. genitalium* nucleic acid is preferably carried out as described above. In this regard, the amplification is preferably carried out by contacting the sample with forward and reverse oligonucleotide primers as described above. Said primers bind to target sites in the *M. genitalium* nucleic acid, under conditions suitable to promote amplification of a nucleic acid sequence comprising at least the target sequence to which the probe binds within SEQ ID NO: 1.

The present invention enables quantitative estimates of pathogen load to be determined. Determining pathogen load has many useful applications, such as for clinical guidance and for determining therapy.

Thus, in one aspect, the present invention provides a method of quantitating *M. genitalium* pathogen load in a sample of interest, comprising: (a) carrying out a detection method according to the present invention on said sample of interest; and (b) carrying out said method on a test sample of predetermined known *M. genitalium* pathogen load; and (c) comparing the signal detected from the sample of interest with the signal detected from the test sample; and thereby quantitating *M. genitalium* pathogen load in the sample of interest.

In another aspect, the method of the present invention is useful for determining efficacy of a course of treatment over a period of time, for example a course of drug therapy.

Thus, in one aspect, the present invention provides an in vitro method of determining drug efficacy over the course of a period of drug therapy, comprising: (a) carrying out the present method on a first sample obtained at a first time point within or prior to the period of drug therapy; (b) carrying out the present method on a sample at one or more later time points within the period of drug therapy; and (c) comparing the signal detected from the first sample with the signal detected from the one or more later samples; and thereby determining drug efficacy over the course of the period of drug therapy.

In one aspect, the method of the present invention is useful for detecting and/or monitoring the development of resistance to a drug (e.g. an anti-microbial such as an antibiotic for *M. genitalium*) over a period of time.

Thus, in one aspect, the present invention provides an in vitro method of detecting and/or monitoring the development of resistance of *M. genitalium* to a drug, comprising (a) carrying out the present method on a first sample obtained at a first time point within or prior to exposure of the *M. genitalium* to the drug; (b) carrying out the present method on a sample at one or more later time points following exposure of the *M. genitalium* to the drug; and (c) comparing the signal detected from the first sample with the signal detected from the one or more later samples; wherein the absence of a reduction in the signal, or an increase in the signal, indicates that the *M. genitalium* have developed resistance to the drug.

In one aspect, the method of the present invention is useful for screening human semen and/or human eggs prior to artificial insemination, to confirm the presence or absence of *M. genitalium*. In this regard, confirmation of the absence of *M. genitalium* infection may be required prior to IVF treatment. Hence, the method of the present invention advantageously reduces (and preferably substantially eliminates) the risk of transmitting *M. genitalium* to a patient undergoing in vitro fertilisation (IVF) treatment.

Thus, in one aspect, the present invention provides an in vitro method of screening a sample comprising human semen and/or eggs for *M. genitalium*, comprising carrying out the present detection method; wherein the absence of a signal indicates that the sample is free of *M. genitalium*.

The detection method of the present invention may also be useful for screening people undergoing IVF treatment, and surrogate mothers, for *M. genitalium* infection.

The detection method of the present invention may also be useful for occupational screening for *M. genitalium* infection. The detection method of the present invention may also be useful for forensic testing e.g. in rap, sexual assault or child abuse cases.

The invention also provides reagents for use in the above-described methods of the present invention.

Hence, the present invention provides a forward primer as described above for use in accordance with the invention. The present invention also provides a reverse primer as described above for use in accordance with the invention. The present invention also provides a pair of forward and reverse oligonucleotide primers selected from the primers described above in accordance with the invention.

The present invention provides a probe as described above for use in accordance with the present invention.

Also provided by the present invention is a kit for detecting *M. genitalium* nucleic acid, comprising a forward primer as described above. Optionally, the kit includes a reverse primer as described above. Optionally, the kit includes a probe as described above.

The present invention is discussed in more detail by means of the Examples described below, and by the Figures.

BRIEF DESCRIPTION OF THE DRAWINGS

FIG. 1 illustrates the relationship between the Mg219 gene (SEQ ID NO: 1), probe SEQ ID NO: 3, forward primer SEQ ID NO: 4, 8 or 31, and reverse primer SEQ ID NO: 5.

In more detail, FIG. 1 illustrates the 447 nucleotide sequence SEQ ID NO: 1 with 3 superimposed shaded regions representing the target/binding sites for the probe SEQ ID NO: 3, the forward primer SEQ ID NO: 4, 8 or 31, and the reverse primer SEQ ID NO: 5. In this regard, although the probe SEQ ID NO: 3 and the forward primer SEQ ID NO: 4, 8 or 31 bind to the complement of SEQ ID NO: 1, for the sake of clarity, the target sites of the probe and forward primer are illustrated with reference to SEQ ID NO: 1.

Thus, the first shaded region represents the target site to which the forward primer SEQ ID NO: 4, 8 or 31 binds, i.e. nucleotide residues –11 to 18 of the complement of SEQ ID NO: 1. The second shaded region represents the target site for the probe SEQ ID NO: 3, i.e. nucleotide residues 66-82 within the complement of SEQ ID NO: 1. The third shaded region represents the target site to which the reverse primer SEQ ID NO: 5 binds, i.e. nucleotide residues 214 to 240 of SEQ ID NO: 1.

Thus, FIG. 1 illustrates that using a forward primer of SEQ ID NO: 4, 8 or 31, and a reverse primer of SEQ ID NO: 5, the resulting amplicon is 251 nucleotides long (spanning nucleotide residue –11 to nucleotide residue 240).

Figure 2:
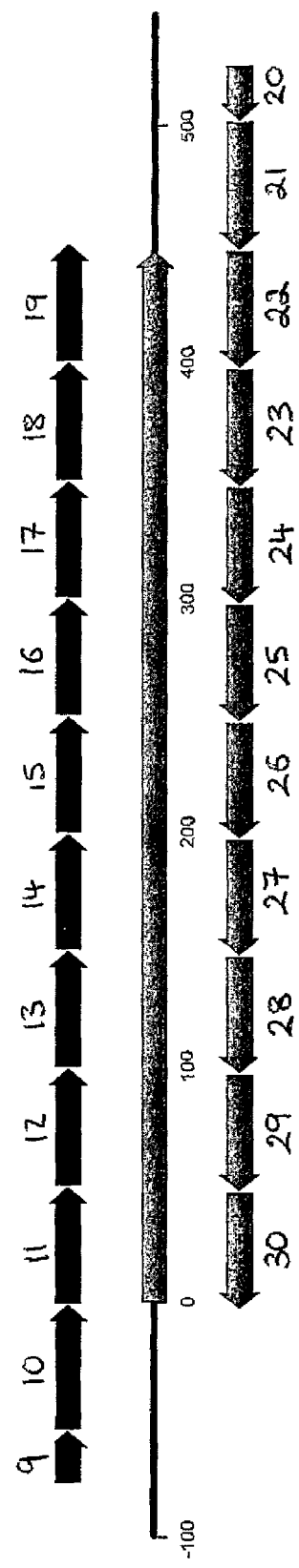

FIG. 2 illustrates the relationship between the Mg219 gene (SEQ ID NO: 1), forward primers SEQ ID NOs: 9-19 and reverse primers SEQ ID NOs: 20-30.

In more detail, FIG. 2 illustrates the 447 nucleotide sequence of Mg219—i.e. SEQ ID NO: 1 (central shaded bar, annotated every 100 nucleotides) plus 100 upstream nucleotides and over 500 downstream nucleotides. Shaded arrows 9 and 20 represent the target/binding sites for the upstream and downstream sequencing primers SEQ ID NOs: 9 and 20, respectively. Shaded arrows 10-19 represent the target/binding sites for the forward primers SEQ ID NOs: 10-19. Shaded arrows 21-30 represent the target/binding sites for the reverse primers SEQ ID NOs: 21-30. In this regard, although the forward primers bind to the complement of SEQ ID NO: 1, for the sake of clarity, the target sites of the forward primer are illustrated with reference to SEQ ID NO: 1.

Thus, it is evident from FIG. 2 that primer SEQ ID NOs: 9 and 10 bind to target sequences located entirely within nucleotide sequences that are upstream of the complement of the Mg219 nucleic acid sequence. Likewise, primer sequences 20 and 21 bind to target sequences located entirely within nucleotide sequences that are downstream of the Mg219 nucleic acid sequence. In contrast, primer SEQ ID NOs: 11-18 bind to target sequences located entirely within the complement of the Mg219 nucleic acid sequence, and primer SEQ ID NOs: 22-29 bind to target sequences located entirely within the Mg219 nucleic acid sequence. However, the target site for primer SEQ ID NO: 19 overlaps the complement of the Mg219 nucleic acid sequence and (3) nucleotides located downstream of the complement of the Mg219 nucleic acid sequence. Likewise, the target site for primer SEQ ID NO: 30 overlaps the Mg219 nucleic acid sequence and (3) nucleotides located upstream of the complement of the Mg219 nucleic acid sequence.

Figure 3:
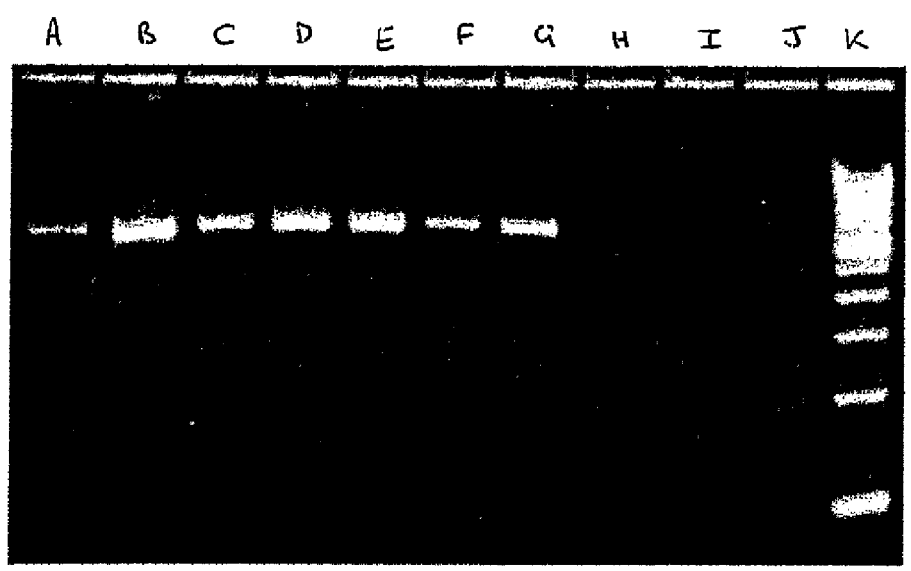

FIG. 3 illustrates the results of gradient PCR to determine optimal annealing temperature using primer sequences SEQ ID NO: 9 and SEQ ID NO: 20. The temperatures tested are as follows: A=57.0° C., B=57.3° C., C=58.0° C., D=58.8° C., E=60.1° C., F=61.8° C., G=63.6° C., H=65.5° C., I=66.4° C., J=67.2° C., K=control.

Figure 4:
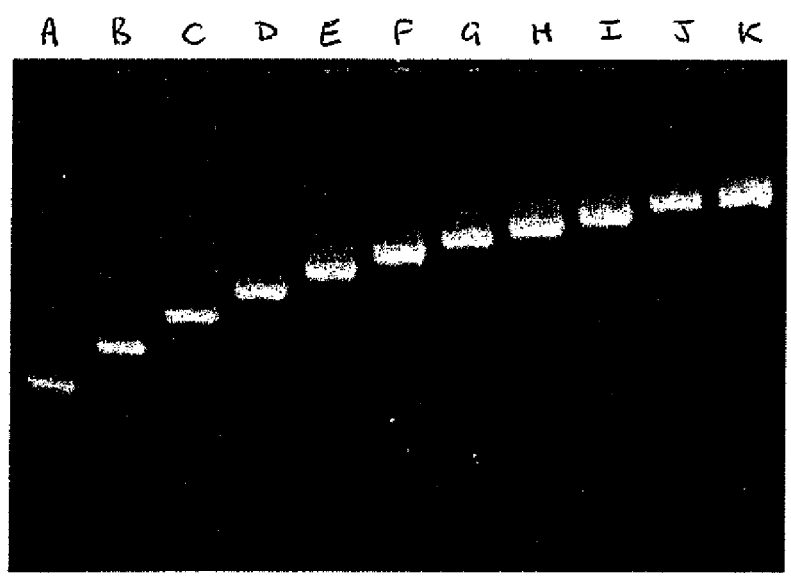

FIG. 4 illustrates detection of the entire Mg219 gene using a span of oligonucleotide primers (forward primer SEQ ID NO: 9 with reverse primers selected from SEQ ID NOs: 20-30) across the full gene sequence. The primer pairs employed are as follows:
    A=SEQ ID NO: 9 plus SEQ ID NO: 30
    B=SEQ ID NO: 9 plus SEQ ID NO: 29
    C=SEQ ID NO: 9 plus SEQ ID NO: 28
    D=SEQ ID NO: 9 plus SEQ ID NO: 27
    E=SEQ ID NO: 9 plus SEQ ID NO: 26
    F=SEQ ID NO: 9 plus SEQ ID NO: 25
    G=SEQ ID NO: 9 plus SEQ ID NO: 24
    H=SEQ ID NO: 9 plus SEQ ID NO: 23
    I=SEQ ID NO: 9 plus SEQ ID NO: 22
    J=SEQ ID NO: 9 plus SEQ ID NO: 21
    K=SEQ ID NO: 9 plus SEQ ID NO: 20

Figure 5:
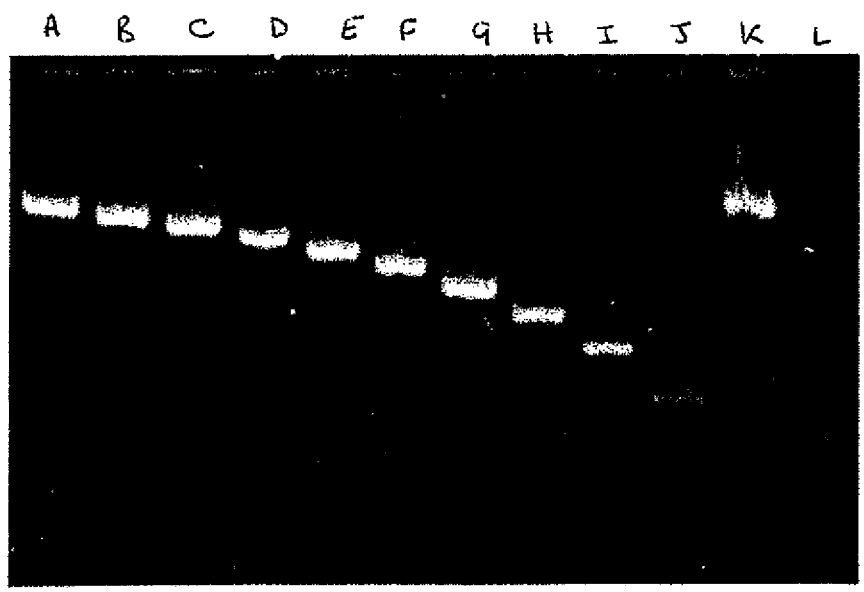
Figure 6:
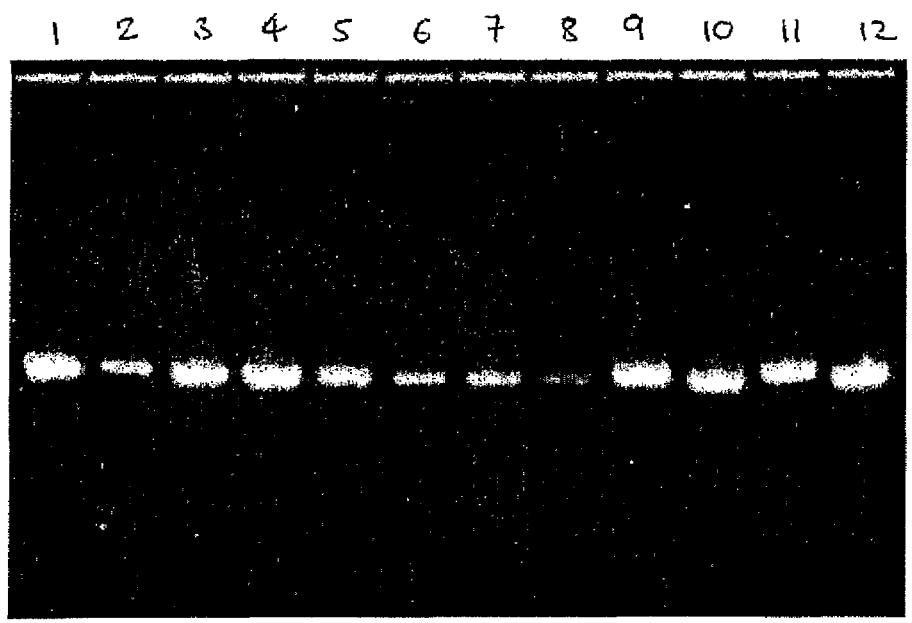

FIG. 5 illustrates detection of the entire Mg219 gene using a span of oligonucleotide primers (reverse primer SEQ ID NO: 20 with forward primers selected from SEQ ID NOs: 9-19) across the full gene sequence. The primer pairs employed are as follows:
    A=SEQ ID NO: 20 plus SEQ ID NO: 10
    B=SEQ ID NO: 20 plus SEQ ID NO: 11
    C=SEQ ID NO: 20 plus SEQ ID NO: 12
    D=SEQ ID NO: 20 plus SEQ ID NO: 13
    E=SEQ ID NO: 20 plus SEQ ID NO: 14
    F=SEQ ID NO: 20 plus SEQ ID NO: 15
    G=SEQ ID NO: 20 plus SEQ ID NO: 16
    H=SEQ ID NO: 20 plus SEQ ID NO: 17
    I=SEQ ID NO: 20 plus SEQ ID NO: 18
    J=SEQ ID NO: 20 plus SEQ ID NO: 19
    K=SEQ ID NO: 20 plus SEQ ID NO: 9
    L=Negative control FIG. 6 illustrates amplification of Mg219 from 12 cultured *M. genitalium* strains (identified as 1-12, see Example 5 for key), using the primer pair SEQ ID NO: 9 and SEQ ID NO: 20.

Figure 7:
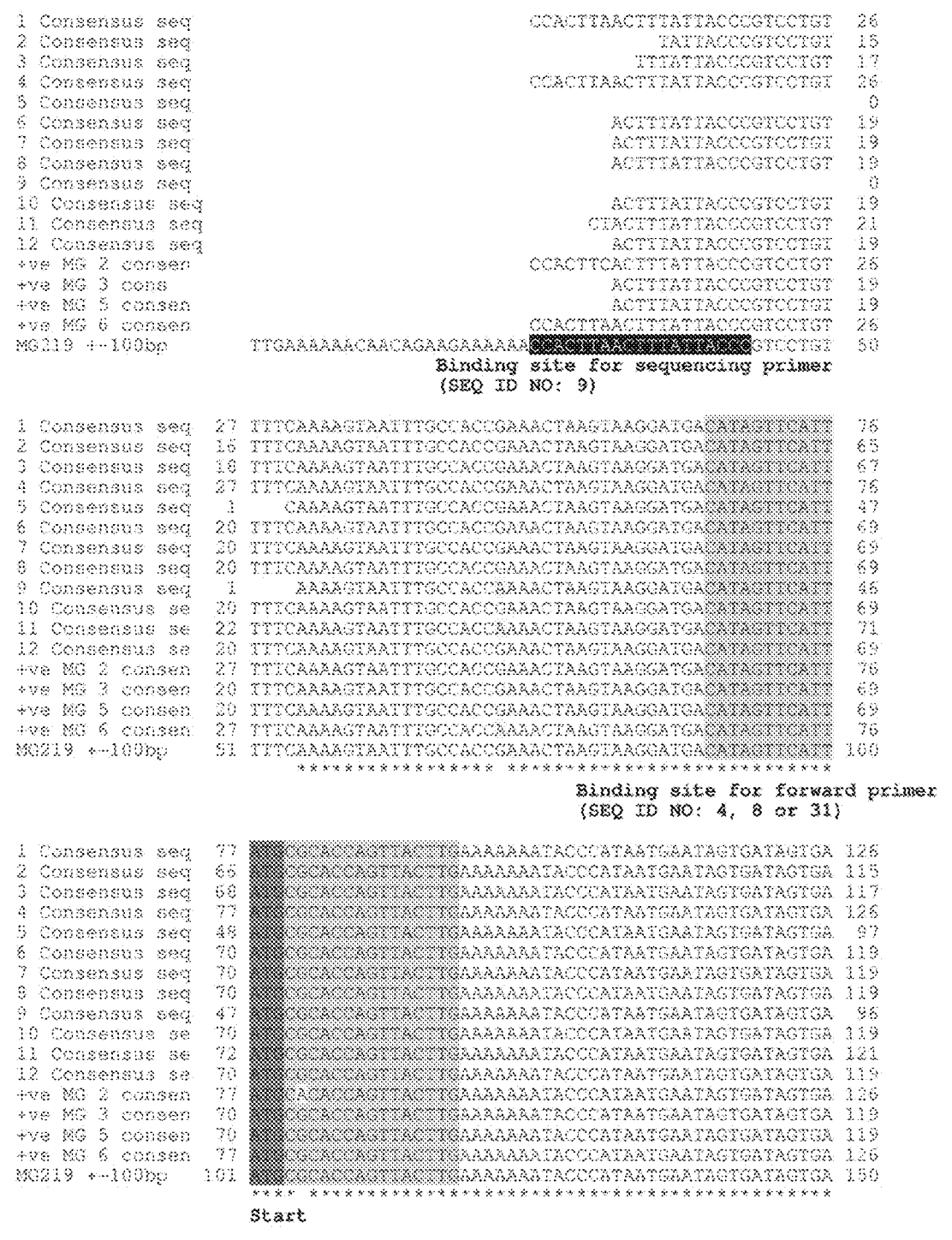
Figure 7:
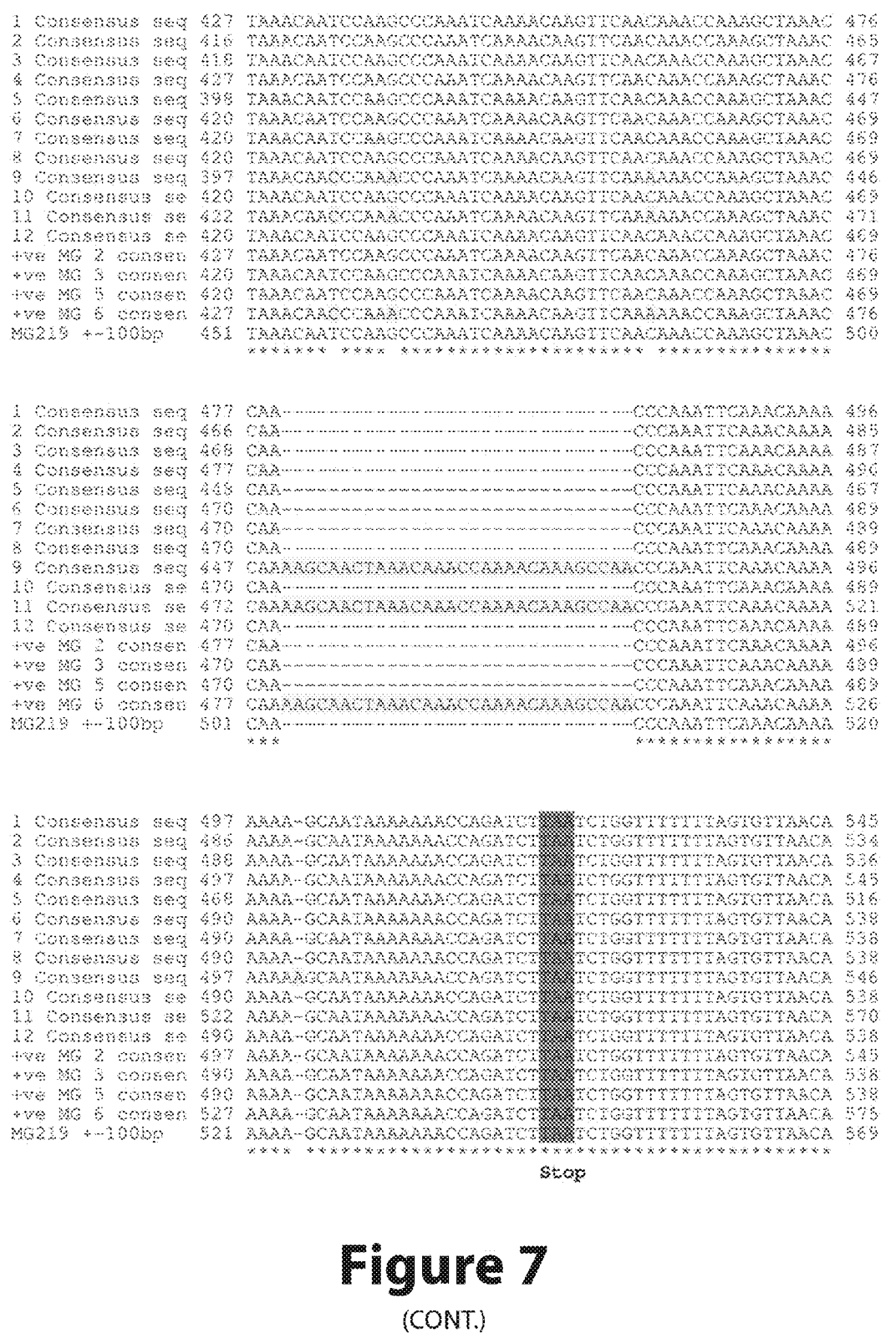

FIG. 7 presents an alignment of the Mg219 gene (plus upstream and downstream nucleotides) from *M. genitalium* strain G37 plus 16 cultured isolates, illustrating the binding sites for the forward and reverse sequencing primers (SEQ ID NOs: 9 and 20), the forward assay primer (SEQ ID NO: 4, 8 or 31), the reverse assay primer (SEQ ID NO: 5) and the probe (SEQ ID NO: 3). Each of the aligned sequences has been allocated a SEQ ID NO: (see Example 5, below). Briefly the cultured isolates are identified as follows: isolate number 1, SEQ ID NO: 32; isolate number 2, SEQ ID NO: 33; isolate number 3, SEQ ID NO: 34; isolate number 4, SEQ ID NO: 35; isolate number 5, SEQ ID NO: 36; isolate number 6, SEQ ID NO: 37; isolate number 7, SEQ ID NO: 38; isolate 8, SEQ ID NO: 39; isolate 9, SEQ ID NO: 40; isolate 10, SEQ ID NO: 41; isolate number 11, SEQ ID NO: 42; isolate number 12, SEQ ID NO: 43; +ve MG2, SEQ ID NO: 44; +ve MG3, SEQ ID NO: 45; +ve MG5, SEQ ID NO: 46; +ve MG6, SEQ ID NO: 47; G37, SEQ ID NO: 48.

FIG. 8 is a ClustalW (v1.4) multiple sequence alignment matrix, illustrating the sequence identity level between the Mg219 sequences (plus up- and down-stream nucleotides) illustrated in FIG. 7. Alignment Score=477772, Gaps Inserted=30, Conserved Identities=549. Pairwise Alignment Mode: Fast. Pairwise Alignment Parameters: ktup=1, Gap Penalty=3, Top Diagonals=5 Window Size=5. Multiple Alignment Parameters: Open Gap Penalty=10.0, Extend Gap Penalty=0.1, Delay Divergent=40% Transitions: Weighted.

EXAMPLES

Example 1

Standard Operating Procedure for Detecting *M. genitalium* Mg219 Gene

This Example details the procedures for the detection of *M. genitalium* Mg219 gene DNA from clinical material or cultures by Polymerase Chain Reaction (PCR) using fluorescent probes on the Corbett Rotor-gene real-time PCR machine.

Gloves and safety glasses were worn throughout, and all extraction procedures were carried out in a Class 1 Safety cabinet. Lower respiratory tract specimens such as sputa and lung biopsies were handled in a CL3 facility while other samples were processed in a Class 1 Safety Cabinet.

Preparing and Running the PCR

Immediately prior to loading tubes into the Rotor-gene PCR machine, the template sample was added to the mixture in a designated PCR cabinet in the PCR clean room. PCR tubes containing mixtures prepared for cycling were capped before leaving the cabinet and conveyed to the Rotor-gene.

Materials
    Sterile screw cap 1.5 mL microfuge plastic tubes
    Sputasol™. (Oxoid) freshly diluted in water (Sigma)
    QIA-Amp DNA Mini Kit. (Qiagen cat no 51306)
    Gilson pipettes: P1000, P200, P20, P10 (or equivalent)
    Pre-sterile tips with filters for above (Rainin)
    Corbett Rotagene Realtime PCR machine
    0.5 mL PCR tubes (flat top)
    Tris-EDTA (TE) buffer 100× concentrate (Sigma cat no T9285)
    AmpliTaq Gold® DNA Polymerase, with GeneAMP (Applied Biosystems cat no 4311820)

AmpErase® Uracil N-glycosylase (UNG) (Applied Biosystems cat no N8080096)

Heating block 56±2° C.

Primers and probes: Adjusted to give 100 μM stock solutions, aliquoted (504) and stored at −30° C. or below.

*M. genitalium* NCTC 10195$^T$ (Positive control) cloned stocks of DNA template (pGEMT-EASY genit219 POS 1, 2, 3, 4 or 5 in *E. coli* TOP10$^{F1}$)

GeneQuant.II (Pharmacia Biotech)

Nuclease-free water (Promega cat no P119C)

Herring sperm DNA dNTP Blend, 12.5 mM with dUTP (Applied Biosystems cat no N8080270)

Procedures

Samples received for PCR may be tested by culture for *Mycoplasmas* and Ureaplasmas (culture samples prior to commencing DNA extraction).

DNA was extracted using a conventional DNA extraction protocol (depending on the circumstances e.g. nature and volume of sample, urgency of request etc. different DNA extraction protocols may be used).

DNA from urine was extracted via centrifugation at 20,000 g for 15 mins, and then the pellet was re-suspended in 0.4 mL PBS and heated at 100° C. for 5 mins (alternatively, the magnapure compact may be used directly on 0.5 mL heat inactivated urine (95° C.±10° C.) without pre-centrifugation). Swabs were extracted by agitating in 0.4 mL PBS and following the same protocol as above.

PBS or water was extracted in tandem with the clinical sample and included in all further tests to ensure cross contamination did not occur.

A 1:10 dilution of the extracted DNA was prepared in nuclease free water. For unusual and highly cellular samples such as tissue a 1:10 and 1:100 dilution was prepared.

Preparation of Cloned *M. genitalium* Standard for Regression Calculation

Because of the problems associated with growing sufficient *Mycoplasma* to generate stocks of standard DNA, a cloned template DNA sequence was prepared.

The concentration and purity of the plasmid solution in TE buffer was estimated using GeneQuant (against TE blank).

The plasmid solution was adjusted to known concentration (100 ng/mL) in Herring sperm DNA at 10 ng/μL (in TE buffer pH 8.0), aliquoted (25 μL), and stored at −20±10° C.

Immediately prior to use, serial dilutions were made (in PCR quality water) to cover the expected dynamic range of the clinical specimens and a water blank. 5 ng, 0.5 ng, 0.05 ng and 0.05 ng serial dilutions were used in each run.

Preparation of Primers and Probes

The primers used in this assay yield a positive product of 251 bp for *M. genitalium* and the probe binds from by 66 to 82 inside the Mg219 gene.

Forward Primer=SEQ ID NO: 4, 8 or 31; Reverse Primer=SEQ ID NO: 5.

Primer aliquots were re-suspended in TE to give 100 pMμL$^{-1}$, aliquoted, assigned batch numbers and stored at −20±10° C. or below.

Probes (SEQ ID NO: 3, [at the 3 nmol scale]) were re-suspended in TE to give 100 pMμL$^{-1}$, aliquoted, assigned batch numbers and stored at −20±10° C.

The probes are light sensitive and should therefore be handled in dark/amber microfuge tubes at all times.

The working primer/probe mix contains 2.5 pmolμL$^{-1}$ (2.5 μM) of each primer, giving a final concentration of 0.5 μM each and 1 pmol μL$^{-1}$ (10 μM) of *M. genitalium* probe, giving a final concentration of 0.2 μM. To make the mix, the following components were added:

| μL | (4 mL total) |
|---|---|
| 3760 | $H_2O$ |
| 100 | Primer Mg219F (SEQ ID NO: 4, 8 or 31) |
| 100 | Primer Mg219R (SEQ ID NO: 5) |
| 40 | Probe Mg219 (SEQ ID NO: 3) |

The primer/probe mix was distributed in 10004 aliquots in black tubes, assigned batch numbers and an expiry date of 12 months and stored at −20±10° C.

Preparation of PCR Reagent Mixture.

A stock mastermix was made for 1000 reactions and aliquoted giving enough mastermix for a full carousel (37 reactions). The stock mastermix was stored at −20±10° C. and given expiry date of 12 months from formation. The reagents were mixed gently by pipetting before use.

| Mastermix | Per sample | Master mix | Final conc. |
|---|---|---|---|
| $H_2O$ | 3.55 μL | 3.55 mL | |
| $MgCl_2$ 25 mM | 4 μL | 4 mL | 5 μM |
| dNTPs 12.5 mM | 1 μL | 1 mL | 0.625 mM |
| Primer/Probe mix | 4 μL | 4 mL | |
| (0.2 μM MG219 probe, 0.5 μM primer) | | | |
| Amplitaq gold 10 × buffer | 2 μL | 2 mL | x1 |
| 538.35 μL were distributed into each tube and frozen at −20 ± 10° C. | | | |
| On day of use 1 vial was defrosted and the following were added to 37 reactions: | | | |
| Amplitaq gold polymerase | 0.25 μL | 9.25 μL | 1.25 unit |
| Uracil-DNA glycosylase | 0.2 μL | 7.4 μL | 1 unit |
| Total | 15 μL | | |

15 μL was distributed into each tube.

All manipulations were performed at 2-8° C. A water blank was included in every PCR experiment. Water was pipetted after other solutions to control for cross contamination. The clinical sample, dilutions and extracted water control were included, pipetted and sealed before adding positive controls.

5 μL of the relevant sample were added and the tubes were closed (giving a final volume of 20 μL). A standard curve of positive control DNA was included. The PCR machine was loaded, making sure that the tubes were closed properly by firmly pressing down the lid and always using the locking rings provided to secure lids on both 0.1 and 0.2 mL tubes.

NOTE: Calibration measures the fluorescence in the 1$^{st}$ tube for all channels and adjusts fluorescence respectively to take account of background. Therefore the first tube must contain all probes used in the assay. Baseline fluorescence should be ~20, for quenched FRET assays where a decrease in fluorescence is expected it should be 50-70. Set calibration to be taken at beginning of first cycle to relevant channel.

Detection of PCR Products

Setting up the Rotorgene PCR Machine:

The PCR machine was set up, samples were put in and the programme was entered/opened. Flat tubes and the required programme channels were set (Cy5—channel 4) and the details of specimens and standards in respective carousel positions were entered. Save and 'start'. The entire carousel was filled with tubes, even if not included in the analysis. The assay was run.

| Cycling conditions 45 cycles | | | | | |
|---|---|---|---|---|---|
| | | Temp | Time | Transition rate | Acquisition mode |
| Denaturation Quantification | | 95° C. | 5 min | 20 secs | None |
| Segment | 1 | 95° C. | 15 sec | 20° C./sec | None |
| | 2 | 60° C. | 60 sec | 20° C./sec | Single |
| Melting Curve | | | | | |
| Segment | 1 | 95° C. | 0 sec | 20° C./sec | None |
| | 2 | 45° C. | 2 sec | 20° C./sec | None |
| | 3 | 80° C. | 0 sec | 0.1° C./sec | Cont |
| Cooling | | | | | |

The Rotor-gene automatically cools

Data Analysis

By clicking the 'analysis' button and double clicking on the Cy5 channel, the software gives the standard curve an efficiency value. If they are unexpectedly high, the assay should be repeated.

Example 2

Validation of the Assay

The purpose of the validation was to determine the following:
1) Specificity—other *Mycoplasma* species and bacterial species from same niche
2) Sensitivity—determine LDL
3) Known positives and negatives
4) Optimal extraction method
5) Alternative PCR platforms
6) Varying sample types
7) Reproducibility
8) Comparison to MgPa assay 1) Specificity

| Species | NCTC/strain identifier | DNA conc | Test result |
|---|---|---|---|
| Commensals | | | |
| *Lactobacillus vaginalis* | 12197 | — | Neg |
| *Prevotella* (Bacteroides) bivius | 11156 | 1 µgmL$^{-1}$ | Neg |
| *Mobiluncus curtisii* | 11657 | — | Neg |
| *Mobiluncus mulieris* | 11658 | 1 µgmL$^{-1}$ | Neg |
| Gp B *Streptococcus* (*S. pyogenes*) | 12067 | — | Neg |
| Gp A *Streptococcus* (*S. algalactiae*) | 12906 | — | Neg |
| *Echerishia. coli* | 9001 | 1 µgmL$^{-1}$ | Neg |
| *Staphylococcus* | 8532 | — | Neg |
| Pathogens | | | |
| *Neisseria gonorrhoea* | H060160180 Clinical sample | — | Neg |
| *Chlamydia trachomatis* | L2, Cell culture DNA | — | Neg |
| *Treponema palidum* | H05510345 Clinical sample | — | Neg |
| *Treponema palidum* | Nichols or Newmarket cell culture strain | — | Neg |
| *Heamophilus ducreyi* | PCR control | — | Neg |
| HSV1 | PCR control | — | Neg |
| Mollicute species | | | |
| *A. laidlawii* | | 1 µgmL$^{-1}$ | Neg |
| *M. hominis* | | 1 µgmL$^{-1}$ | Neg |
| *M. pneumoniae* | | 1 µgmL$^{-1}$ | Neg |
| *M. amphoriforme* | | 1 µgmL$^{-1}$ | Neg |
| *M. fermentans* | | 1 µgmL$^{-1}$ | Neg |
| *M faucium* | | 1 µgmL$^{-1}$ | Neg |
| *M. penetrans* | | 1 µgmL$^{-1}$ | Neg |
| *M. pirum* | | 1 µgmL$^{-1}$ | Neg |
| *M. spermatophilum* | | 1 µgmL$^{-1}$ | Neg |
| *M. primatum* | | 1 µgmL$^{-1}$ | Neg |
| *M. salivarium* | | 1 µgmL$^{-1}$ | Neg |
| *M. buccale* | | 1 µgmL$^{-1}$ | Neg |
| *M. orale* | | 1 µgmL$^{-1}$ | Neg |
| *M. lipophilum* | | 1 µgmL$^{-1}$ | Neg |
| *U. parvum* (Sero 1) | | 1 µgmL$^{-1}$ | Neg |
| *U. urealyticum* (Sero 12) | | 1 µgmL$^{-1}$ | Neg |

Summary—the Assay does not Amplify Other Bacteria or Mollicutes

2) Sensitivity

| Standard conc (µgmL$^{-1}$) | Result | Cp (average) |
|---|---|---|
| 100 | Pos | 15.28, 15.16 (15.22) |
| 10 | Pos | 19.2, 19.07 (19.14) |
| 1 | Pos | 24.37, 21.37 (24.37) |
| −1 | Pos | 27.33, 27.28 (27.3) |
| −2 | Pos | 31.27, 31.41, 31.08, 31.12 (31.22) |
| −3 | Pos | 34.46, 35.33, 34.84, 36.27 (35.17) |
| −4 | Pos | 37.87, 39.17, 38.18, — (38.41) |
| −5 | Neg | 38.56, —, —, — |
| −6 | Neg | —, —, —, — |
| −7 | Neg | —, —, —, — |

LDL Calculations:

The lowest detectable limit of detection was 5 µL of a 10$^{-4}$ dilution of a 1 µgmL$^{-1}$ extract of DNA. This corresponds to 0.0001 µgmL$^{-1}$ or 100 pg, 0.5 pg per 5 µL in reaction and 825 gene copies per reaction. The assay could detect DNA at one further dilution (at 82.5 gene copies per reaction), however reproducibility was then affected.

The assay LDL is =0.5 pg per reaction

The point at which a real-time PCR is determined as positive can be known as a crossing point (Cp). A lower Cp indicates a larger amount of target DNA in the sample or more efficient amplification. For all positive specimens to date the mean Cp was 34 in the Mg219 assay of the present invention, and 36 in the known MgPa assay.

This indicates that the Mg219 assay of the present invention may be more sensitive that the known MgPa assay.

3) Known Positives/Negatives

| Sample type | Sample number/ID | Expected Result (Mg219 assay) | Actual result (MgPa assay) |
|---|---|---|---|
| Urethral isolate (J. Tully) | M30 10-4 | P | P* |
| Urethral isolate (J. Tully) | M 30 early 10-2 | P | P* |
| Human throat (J. Tully) | TW10-5G 10-4 | P | P* |
| Human throat (J. Tully) | TW10-6 G10-4 | P | P* |
| Human Throat (J. Tully) | R-32G 10-3 | P | P* |
| Human throat (J. Tully) | TW 48-5G 10-4 | P | P* |
| Urethra (J. Jensen) | M 2300 10-4 | P | P* |

-continued

| Sample type | Sample number/ID | Expected Result (Mg219 assay) | Actual result (MgPa assay) |
|---|---|---|---|
| Urethra (J. Jensen) | M2321 10-3 | P | P* |
| Urethra (J. Jensen) | M2341 10-3 | P | P* |
| Urethral isolate (D. T. Robinson) | G37 10-4 | P | P* |
| Urethra (J. Jensen) | M 2288 10-3 | P | P* |
| Synovial fluid (J. Tully) | UTMB-10G 10-4 | P | P* |
| Water | N/A | N | N |
| PBS | N/A | N | N |

P = positive in Jensen et al. (2004) publication
Summary - all known positives are detected.
Known negatives are not reactive in the assay 4) Optimal Extraction Method Extraction of *M. hominis* spiked urine was performed using varying methods (boiling, qiagen, magnapure compact). The magnapure compact gave the optimal results.

Samples are best stored at 4° C., not at room temperature.

DNA was detectable for up to 28 days.

The addition of RND/DNA protect enhances detection and eliminates the temperature differences—but does not alter results and is not therefore cost effective.

Concentration of sample prior to extraction of DNA is recommended.

5) Alternative PCR Platforms

The Mg219 assay has been tested on the Roche Lightcycler and the ABI Taqman 7700. The assay performed satisfactorily on both platforms (positive controls were amplified and detected whilst negative controls were not).

These results indicate that the chemistry used in the Mg219 assay is transferable to other real-time platforms.

6) Varying Sample Types (Comparison with MgPa Assay)

| Sample | Mg219 (actual result) | MgPa assay (expected result) |
|---|---|---|
| Urine | 0/112 positive | 0/112 positive (1 FP) |
| Rectal swabs | 2/22 positive | 2/22 positive |
| Anal swab | 0/1 positive | 0/1 positive |
| Urethral swabs | 0/13 positive | 0/13 positive |
| Genital ulcer swabs | 0/18 positive | 0/18 positive |
| Penile swab | 1/1 positive | 0/1 positive |
| Liquid based cytology samples - cervical swab | 0/30 positive | 0/30 positive |
| Vaginal swabs | 0/35 positive | 0/35 positive |
| Respiratory samples | 0/38 positive | 0/38 positive (1 FP) |
| Endocervical samples | 5/309 positive | 5/309 positive (7 FP) |
| Defined samples total | 8/579 positive (1.38%) | 7/579 positive (1.21%) (9 FP) |

FP-false positive - specimens positive only in the MgPa assay are thought to be false positive results (see below).

7) Reproducibility

Mg219 controls, CT values when run on several days

| Date | Expt number | 1/10 | 1/100 | 1/1000 |
|---|---|---|---|---|
| 16/2/6 | 0236 | 13.86 | 17.17 | 22.8 |
| 17/2/6 | 0240 | 12.39 | 16.89 | 22.23 |
| 24/2/6 | 0247 | 11.24 | 16.63 | 22.14 |
| 02/3/6 | 0249 | 10.99 | 17.21 | 24.01 |
| 03/3/6 | 0251 | 12.83 | 19.08 | 23.84 |
| 7/4/6 | 0255 | 11.66 | 17.44 | 23.23 |
| 11/5/6 | 0258 | 12.84 | 15.81 | 19.31 |
| | AVERAGE | 12.26 | 17.18 | 22.51 |
| | STDEV | 1.02 | 1.00 | 1.59 |
| | Boundaries (+/−2 × STDEV) | 10.22-14.30 | 15.19-19.17 | 19.34-25.68 |

Note all runs are within average +/− 2 × STDEV.

8) Comparison to Known MgPa Assay (Jensen et al., 2004)

| | Known MgPa assay | New HPA MG219 assay |
|---|---|---|
| Specificity | Does not cross react with any human Mycoplasma species | Does not cross react with any human Mycoplasma species |
| | Does not cross react with bacteria and viruses listed above | Does not cross react with bacteria and viruses listed above Gene and primers/probes do not align to any other genes with significant homology on search of BLAST and other public databases Using ORFANAGE program MG219 is found only in *M. genitalium* and not in other published whole genome sequences Using MOLLIGEN whole genome comparison, MG219 is not found in any other Mycoplasma species. |
| Sensitivity | Lower detection limit = 0.5 pg per reaction of *M. genitalium* DNA. | Lower detection limit = 0.5 pg per reaction of *M. genitalium* DNA (same as MgPa assay). |
| Known positives | Detects all known positives tested (culture positive) | Detects all known positives tested (culture positive) |
| Known negatives | Does not amplify known negatives | Does not amplify known negatives |

-continued

| Sample | MgPa assay (expected result) | Mg219 (actual result) |
|---|---|---|
| Urine | 0/112 pos (1FP) | 0/112 pos |
| Rectal swabs | 2/22 pos | 2/22 pos |
| Anal swab | 0/1 pos | 0/1 pos |
| Urethral swabs | 0/13 pos | 0/13 pos |
| Genital ulcer swabs | 0/18 pos | 0/18 pos |
| Penile swab | 0/1 pos | 1/1 pos (1FP) |
| LBC samples - cervical swab | 0/30 pos | 0/30 pos |
| Vaginal swabs | 0/35 pos | 0/35 pos |
| Respiratory samples | 0/38 pos (1FP) | 0/38 pos |
| Endocervical samples | 5/309 pos (7FP) | 5/309 pos |
| Defined samples total | 7/579 pos (9FP) | 8/579 pos (1FP) |
| Undefined samples (query type) | 4/155 pos (11FP) | 4/155 (0FP) |

Example 3

Epidemiological Data (UK Population)

To date, 548 specimens have been tested, of which 9 (1.65%) were positive in the MG219 assay (see Table below). This indicates a level of approximately 1.65% infected individuals within the UK population.

Epidemiological information from research study specimens

| | Mg219 (actual result) | Known MgPa assay (expected result) |
|---|---|---|
| Cornwall NHS Trust | 0/134 pos (0%) | 0/134 pos (3 FP) |
| University Hospital College London | 5/274 pos (1.82%) | 5/274 (5 FP) |
| Northampton General Hospital | 4/140 pos (2.86%) | 4/140 pos (6 FP) |
| Research study specimens total | 9/548 pos (1.65%) | 9/548 pos (14 FP) |

The samples are taken from both symptomatic and asymptomatic patients and therefore the true level of infection in specific clinical groups (such as those without symptoms or with urethritis) may be lower or higher than reflected herein. Also, these samples are in the main from 3 geographical areas (Cornwall, London, Northampton) with levels varying from 0%, 1.82% to 2.86%. Larger scale screening will indicate if geographical differences occur in infection levels.

False Positive Specimens in the Known MgPa Assay:

To date we have 20 specimens which are positive according to the MgPa assay described by Jensen et al. (2004) and negative in the Mg219 assay of the present invention. On repeat testing only 2 of the 20 were positive in the MgPa test, which indicates that they are likely to be false positives in the Jensen et al. MgPa test. In this regard, the present inventors have been unable to repeat the MgPa positive result and have not had any positives using two other PCR methods (Cadieux N. et al., (1993) J Gen Microbiol. 1993 October; 139(10): 2431-7, and MG192 PCR by Musatovova O. et al., (2006) J Clin Microbiol. 44(2):598-603).

The mean Cp for these samples was 39, which could be indicative of inefficient amplification due to either lower amounts of target DNA or non-specific amplification. The former is unlikely, because all samples positive in both assays had lower mean Cp in the MG219 assay of the present invention than in the known MgPa assay.

This indicates that the Mg219 assay of the present invention is more sensitive than the known MgPa assay for the detection of *M. genitalium*.

Example 4

Further Primer Design

A. Designing Primers for PCR of Whole of MG219

Two primers were designed binding upstream and downstream of the Mg219 nucleic acid sequence. As illustrated in the Table below, the up-stream, forward primer SEQ ID NO: 9 mapped to position −76 to −54 (upstream of the start codon) and the downstream, reverse primer SEQ ID NO: 20 mapped to position 503 to 525 (downstream of the stop codon) of MG219. The annealing temperature of the primers was calculated using the formula: Tm=4*(number of G's and C's)+ 2*(number of A's and T's).

| Primer | Sequence | Position |
|---|---|---|
| SEQ ID NO: 9 | CCACTTAACTTTATTACCCGTCC | −76 to −54 |
| SEQ ID NO: 20 | GATTAACCCCAGGTAGTTCTTCC | +503-525 |

To confirm the suitability of the primers, BLAST analysis was carried out for each of the primers against the *M. genitalium* G37 genome. Selecting the "Advanced Blast" parameters, small primer sequences showed unique binding sites and enabled determination of homologous sequences elsewhere on the genome, and prediction of possible multiple amplification products upon PCR.

B. Determining Optimum Annealing Temperature for PCR

To optimise the annealing temperature and avoid multiple PCR products, gradient PCR was performed using the primers SEQ ID NO: 9 and SEQ ID NO: 20, ranging from 57-68° C. This was performed on a MJ Research DNA engine, which does not perform a linear gradient across the block (FIG. 3).

No other products were observed—indicating that only the MG219 gene was amplified. The resulting amplicons were used to determine the sequence of the MG219 gene and to amplify across the gene.

C. Detection of Mg219

Forward primers SEQ ID NOs: 10-19 were designed starting from position −53 relative to the start codon and mapping consecutively to 3 bases beyond the stop codon, to cover the entire gene sequence of Mg219 (see Table below).

| Forward Primer SEQ ID NOs: | Sequence | Position |
|---|---|---|
| 10 | TGTTTTCAAAAGTAATTTGCCACCGAAACTAAGTAAGGATGACATAGTTCATT | −53 to −1 |
| 11 | ATGCGCACCAGTTACTTGAAAAAAATACCCATAATGAATAGTGATAGTGA | 1-50 |
| 12 | TCTAAAACTCCAAAAGGTGTGGATCGAGCGGCATGTTGATCAAGATGAAC | 51-100 |
| 13 | TTAGTTTAACAACTACTGCAGTTGAACTTAAAAAGAGTGATGAACAAAAA | 101-150 |
| 14 | CCTGTTGCCATTAAAAGTAGTGACTTTATTGGTCATGAAGAGTTAATCTC | 151-200 |
| 15 | TGTTCCAGTTTTACTAATCCCAACCCCTGTTGTTAAAGAGATTGATCAAC | 201-250 |
| 16 | CAGCAGTTATTCCTCCAGTTAAAGCAAAACCAAAAGCAACTAAAAAGAAA | 251-300 |
| 17 | ACTCCTGTTAAATCAAAACCAACTAGTAAATCAACTAAACAAACAAAACC | 301-350 |
| 18 | TAAACAATCCAAGCCCAAATCAAAACAAGTTCAACAAACCAAAGCTAAAC | 351-400 |
| 19 | CAACCCAAATTCAAACAAAAAAAGCAATAAAAAAACCAGATCTTAATCT | 401-+450 |

Reverse primer SEQ ID NOs: 21-30 were designed starting from position +502 from the start codon and they map consecutively upstream towards the start codon (see Table below).

| Reverse Primer SEQ ID NOs: | Sequence | Position |
|---|---|---|
| 21 | TATTCCTTTCCAGTTTTTAGTTAAAACTACTGTTGTTAACACTAAAAAACCAGA | +448-+502 |
| 22 | TTAAGATCTGGTTTTTTTATTGCTTTTTTTGTTTGAATTTGGGTTGGTT | 398-447 |
| 23 | TAGCTTTGGTTTGTTGAACTTGTTTTGATTTGGGCTTGGATTGTTTAGGT | 348-397 |
| 24 | TTTGTTTGTTTAGTTGATTTACTAGTTGGTTTTGATTTAACAGGAGTTTT | 298-347 |
| 25 | CTTTTTAGTTGCTTTTGGTTTTGCTTTAACTGGAGGAATAACTGCTGGTT | 248-297 |
| 26 | GATCAATCTCTTTAACAACAGGGGTTGGGATTAGTAAAACTGGAACAGAG | 198-247 |
| 27 | ATTAACTCTTCATGACCAATAAAGTCACTACTTTTAATGGCAACAGGTTT | 148-197 |

| Reverse Primer SEQ ID NOs: | Sequence | Position |
|---|---|---|
| 28 | TTGTTCATCACTCTTTTTAAGTTCAACTGCAGTAGTTGTTAAACTAAGTT | 98-147 |
| 29 | CATCTTGATCAACATGCCGCTCGATCCACACCTTTTGGAGTTTTAGATCA | 48-97 |
| 30 | CTATCACTATTCATTATGGGTATTTTTTCAAGTAACTGGTGCGCATAAT | −3-47 |

Individual PCRs were performed using forward primer SEQ ID NO: 9 plus any one of reverse primers SEQ ID NOs: 21-30; and also using forward primer SEQ ID NO: 20 plus any one of reverse primers SEQ ID NOs: 10-19.

As illustrated in FIGS. 4 and 5, PCR amplification using the primer pairs described above detected the whole Mg219 gene.

Example 5

Conservation of the Mg219 Gene

PCR amplification of the entire Mg219 gene and flanking regions (upstream and downstream sequences) was performed using primers SEQ ID NO: 9 and SEQ ID NO: 20 on twelve cultured *M. genitalium* isolates (see Table below) and the type strain MG37 using Roche High Fidelity Taq.

The resultant amplified fragments were all of the same size (except isolates 9 and 11, which appeared slightly larger on agarose gel electrophoresis) see FIG. 6.

| Cultured Isolate Number | *M. genitalium* strain name | Origin |
|---|---|---|
| 1 | M30 10-4 | Urethra |
| 2 | M30 early 10-2 | Urethra |
| 3 | TW10-5G 10-4 | Throat |
| 4 | TW10-6G 10-4 | Throat |
| 5 | R-32G 10-3 | Throat |
| 6 | TW48-5G 10-4 | Throat |
| 7 | M2300 10-4 | Urethra |
| 8 | M2321 10-3 | Urethra |
| 9 | M2341 10-3 | Urethra |
| 10 | G37 10-4 | Urethra |
| 11 | M2288 10-3 | Urethra |
| 12 | UTMB 10G 10-4 | Synovial fluid |
| G37 | NCTC type strain | Urethra |

The resulting amplified fragments were purified and the concentrations determined. Both strands of the PCR products were sequenced using the oligonucleotide primers SEQ ID NO: 9 and SEQ ID NO: 20 in triplicate. Sequencing was performed using the Becton-Dickinson sequencing kit following the manufacture's instructions and using the CEQ8000 DNA sequencer instrument and the consensus sequence for each strain was determined using MapVector and ClustalW software.

Sequences were aligned and the alignment showed high conservation of the MG219 gene (see Table below and FIGS. 7 and 8). Only 40 bases differed from the 569 bases of the control G37 strain and these differences were found only within strains 9 and 11. Of these, 30 bases consisted of an insertion in isolates 9 and 11 between residues 504 and 505 of the control strain.

Further subsequent sequence analysis of four positive samples (identified as +ve MG 2, +ve MG 3, +ve MG 5 and +ve MG 6, below) has determined that positive clinical specimens are also highly conserved. The insertion sequence is also present in the sequence from Sample +ve MG 6.

| Isolate Number | SEQ ID NO: | MG219 identity to G37 strain |
| --- | --- | --- |
| 1 | 32 | 100% |
| 2 | 33 | 100% |
| 3 | 34 | 100% |
| 4 | 35 | 100% |
| 5 | 36 | 100% |
| 6 | 37 | 100% |

-continued

| Isolate Number | SEQ ID NO: | MG219 identity to G37 strain |
| --- | --- | --- |
| 7 | 38 | 100% |
| 8 | 39 | 100% |
| 9 | 40 | 93.1% (40/569) |
| 10 | 41 | 100% |
| 11 | 42 | 93.2% (39/569) |
| 12 | 43 | 100% |
| +ve MG 2 | 44 | 99.8% (1/569) |
| +ve MG 3 | 45 | 100% |
| +ve MG 5 | 46 | 100% |
| +ve MG 6 | 47 | 93.2% (39/569) |
| G37 | 48 | N/A |

The invention claimed is:

1. A method for specifically detecting *M. genitalium* nucleic acid including clinical isolate *M. genitalium* nucleic acid in a clinical sample, comprising:
   (a) amplifying a nucleic acid sequence comprising a fragment of SEQ ID NO: 1, wherein said fragment of SEQ ID NO: 1 is at least 25 consecutive nucleotides of SEQ ID NO: 1, by contacting said sample with forward and reverse primers, to produce the amplified nucleic acid sequence;
   wherein said forward primer binds to a target site located between nucleotide residue 41 and nucleotide residue 125 of the nucleic acid strand complementary to SEQ ID NO: 48; and
   wherein said reverse primer binds to a target site located between nucleotide residue 197 and nucleotide 350 of SEQ ID NO: 48;
   (b) detecting the amplified nucleic acid sequence; and
   (c) detecting specifically *M. genitalium* nucleic acid including *M. genitalium* nucleic acid from clinical isolates in the clinical sample, based on the presence of said amplified nucleic acid sequence.

2. The method according to claim 1, wherein said forward and reverse oligonucleotide primers are at least 20 nucleotides long.

3. The method according to claim 1, wherein said detecting step comprises:
   (a) contacting said amplified nucleic acid sequence with a probe, wherein the probe binds to a target site within said amplified nucleic acid sequence, or the complement thereof; and
   (b) detecting binding of said probe to said amplified nucleic acid sequence.

4. The method according to claim 3, wherein the probe binds to a target site located between nucleotide residues 55 and 100 of the nucleic acid strand complementary to SEQ ID NO: 1.

5. The method according to claim 3, wherein said probe is at least 15 nucleotides long and up to 50 nucleotides long.

6. The method according to claim 5, wherein the probe comprises the nucleic acid sequence of SEQ ID NO: 3, or a fragment thereof having at least 15 nucleotides.

7. An in vitro method for quantitating specifically *M. genitalium* pathogen load including clinical *M. genitalium* isolates in a clinical sample, comprising:
   (a) amplifying a nucleic acid sequence comprising a fragment of SEQ ID NO:1, wherein said fragment of SEQ ID NO: 1 is at least 25 consecutive nucleotides of SEQ ID NO:1, by contacting the clinical sample and a reference sample having a predetermined known *M. genitalium* pathogen load with forward and reverse primers,
   wherein said forward primer binds to a target site located between nucleotide residue 41 and nucleotide residue 125 of the nucleic acid stand complementary to SEQ ID NO: 48; and wherein said reverse primer binds to a target site located between nucleotide residue 197 and nucleotide 350 of SEQ ID NO: 48;
   (b) detecting the amplified nucleic acid sequence in the clinical sample and in the reference sample; and
   (c) determining the quantity of the amplified nucleic acid sequence in the clinical sample and in the reference sample as indicative of the quantity of the *M. genitalium* nucleic acid in the clinical sample and in the reference sample; and
   (d) comparing the quantity of *M. genitalium* nucleic acid detected in the clinical sample with the quantity of *M. genitalium* nucleic acid detected in the reference sample;
   and thereby quantitating specifically *M. genitalium* pathogen load including clinical *M. genitalium* isolates in the clinical sample.

8. An in vitro method for determining the efficacy of a drug against *M. genitalium* and *M. genitalium* clinical isolates over the course of a period of drug therapy, comprising:
   (a) amplifying a nucleic acid sequence comprising a fragment of SEQ ID NO:1, wherein said fragment of SEQ ID NO: 1 is at least 25 consecutive nucleotides of SEQ ID NO:1, by contacting a first clinical sample obtained at a first time point within or prior to the period of drug therapy and a second clinical sample obtained at a later time point within the period of drug therapy with forward and reverse primers,
   wherein said forward primer binds to a target site located between nucleotide residue 41 and nucleotide 125 of the nucleic acid strand complementary to SEQ ID NO: 48; and
   wherein said reverse primer binds to a target site located between nucleotide residue 197 and nucleotide 350 of SEQ ID NO: 48;
   (b) detecting the amplified nucleic acid sequence in the first and second clinical sample;
   (c) determining the quantity of the amplified nucleic acid sequence in the first and second clinical sample as indicative of the quantity of *M. genitalium* nucleic acid and *M. genitalium* clinical isolate nucleic acid in the first and second clinical sample; and
   (d) comparing the quantity of *M. genitalium* nucleic acid and *M. genitalium* clinical isolate nucleic acid detected in the first clinical sample with the quantity of *M. genitalium* nucleic acid and *M. genitalium* clinical isolate nucleic acid detected in the second clinical samples, wherein a decrease in the quantity of *M. genitalium* nucleic acid and *M. genitalium* clinical isolate nucleic acid detected in the second clinical samples as compared to the first clinical sample indicates that the drug has been effective against *M. genitalium* and *M. genitalium* clinical isolate nucleic acid over the course of the period of drug therapy, whereas an increase in the quantity of *M. genitalium* nucleic acid and *M. genitalium* clinical isolate nucleic acid detected in the second clinical samples as compared to the first clinical sample indicates that the drug has been ineffective against *M. genitalium* over the course of the period of drug therapy;
   and thereby determining drug efficacy against *M. genitalium* and *M. genitalium* clinical isolates over the course of the period of drug therapy.

9. An in vitro method for detecting and/or monitoring the development of resistance of *M. genitalium* over the course of a period of drug therapy, comprising:
   (a) amplifying a nucleic acid sequence comprising a fragment of SEQ ID NO:1, wherein said fragment of SEQ ID NO: 1 is at least 25 consecutive nucleotides of SEQ ID NO:1, by contacting a first clinical sample obtained at a first time point within or prior to the exposure of *M. genitalium* to the drug and a second clinical sample obtained at a later time point following exposure of *M. genitalium* to the drug with forward and reverse primers,
   wherein said forward primer binds to a target site located between nucleotide residue 41 and nucleotide 125 of the nucleic acid strand complementary to SEQ ID NO: 48; and wherein said reverse primer binds to a target site located between nucleotide residue 197 and nucleotide 350 of SEQ ID NO: 48;

(b) detecting the amplified nucleic acid sequence in the first and second clinical sample;

(c) determining the quantity of the amplified nucleic acid sequence in the first and second clinical sample as indicative of the quantity of *M. genitalium* nucleic acid in the first and second clinical sample; and (d) comparing the quantity of *M. genitalium* nucleic acid detected in the first clinical sample with the quantity of *M. genitalium* nucleic acid detected in the second clinical samples;

wherein the absence of a reduction in the quantity of *M. genitalium* nucleic acid in the second clinical samples as compared to the first clinical sample, or an increase in the quantity of *M. genitalium* nucleic acid in the second clinical samples as compared to the first clinical sample, indicates that the *M. genitalium* have developed resistance to the drug.

10. The method according to claim 3, wherein said probe is at least 15 nucleotides long and up to 20 nucleotides long.

11. The method according to claim 4, wherein said probe binds to a target site located between nucleotide residues 60 and 90 of the nucleic acid strand complementary to SEQ ID NO: 1.

12. The method according to claim 4, wherein said probe binds to a target site located between nucleotide residues 65 and 85 of the nucleic acid strand complementary to SEQ ID NO: 1.

13. The method according to claim 3, wherein said probe comprises the nucleic acid sequence of SEQ ID NO: 3.

14. The method according to claim 1, wherein said fragment of SEQ ID NO: 1 is at least 100 consecutive nucleotides of SEQ ID NO: 1 or at least 200 consecutive nucleotides of SEQ ID NO: 1.

15. The method according to claim 1, wherein said fragment of SEQ ID NO: 1 is up to 275 consecutive nucleotides of SEQ ID NO: 1.

16. The method according to claim 2, wherein said forward primer and/or said reverse primer is between 25-30 nucleotides long.

17. The method according to claim 2, wherein said forward primer and/or said reverse primer is between 45-55 nucleotides long.

18. The method according to claim 1, wherein said forward primer binds to a target site located between nucleotide residues 1-18 of a nucleic acid strand complementary to SEQ ID NO: 1, and said reverse primer binds to a target site located between nucleotide residues 214-240 of SEQ ID NO: 1.

19. The method according to claim 1, wherein the forward primer target site is located between nucleotide residue 76 and nucleotide residue 125 of a nucleic acid strand complementary to SEQ ID NO: 48.

20. The method according to claim 19, wherein the forward primer target site is located between nucleotide residue 81 and nucleotide residue 120 of a nucleic acid strand complementary to SEQ ID NO: 48.

21. The method according to claim 19, wherein the forward primer target site is located between nucleotide residue 86 and nucleotide residue 120 of a nucleic acid strand complementary to SEQ ID NO: 48.

22. The method according to claim 1, wherein said forward primer binds to a target site that comprises nucleotide residues 101-118 of a nucleic acid strand complementary to SEQ ID NO: 48.

23. The method according to claim 1, wherein said forward primer binds to a target site located from nucleotide residue 90 to nucleotide residue 118 of a nucleic acid strand complementary to SEQ ID NO: 48.

24. The method according to claim 1, wherein the forward primer target site is located between nucleotide residue 41 and nucleotide residue 101 of a nucleic acid strand complementary to SEQ ID NO: 48.

25. The method according to claim 24, wherein the forward primer target site is located between nucleotide residue 46 and nucleotide residue 101 of a nucleic acid strand complementary to SEQ ID NO: 48.

26. The method according to claim 1, wherein said forward primer binds to a target site located from nucleotide residue 48 to nucleotide residue 100 of a nucleic acid strand complementary to SEQ ID NO: 48.

27. The method according to claim 1, wherein said forward primer comprises a nucleic acid sequence having at least 90% sequence identity to a nucleic acid sequence selected from SEQ ID NOs: 4, 8, 10, or 31.

28. The method according to claim 1, wherein said forward primer comprises a nucleic acid selected from SEQ ID NOs: 4, 8, 10, and 31.

29. The method according to claim 1, wherein said forward primer comprises a nucleic acid sequence selected from SEQ ID NOs: 4, 8, and 31, or at least 27 consecutive nucleotides of SEQ ID NOs: 4, 8, or 31.

30. The method according to claim 1, wherein said reverse primer binds to a target site located between nucleotide residue 197 and nucleotide residue 297 of SEQ ID NO: 48.

31. The method according to claim 1, wherein said reverse primer binds to a target site located between nucleotide residue 198 and nucleotide residue 247 of SEQ ID NO: 48.

32. The method according to claim 1, wherein said reverse primer binds to a target site located between nucleotide residue 248 and nucleotide residue 350 of SEQ ID NO: 48.

33. The method according to claim 1, wherein the reverse primer target site is located from nucleotide residue 298 to nucleotide residue 347 of SEQ ID NO: 48.

34. The method according to claim 1, wherein said reverse primer binds to a target site located between nucleotide residue 300 and nucleotide residue 350 of SEQ ID NO: 48.

35. The method according to claim 1, wherein the reverse primer target site is located between nucleotide residue 310 and nucleotide residue 345 of SEQ ID NO: 48.

36. The method according to claim 1, wherein the reverse primer target site is located from nucleotide residue 314 and nucleotide residue 340 of SEQ ID NO: 48.

37. The method according to claim 1, wherein said reverse primer comprises a nucleic acid sequence having at least 90% sequence identity to a nucleic acid sequence selected from SEQ ID NOs: 5, 26, and 28.

38. The method according to claim 1, wherein said reverse primer comprises a nucleic acid sequence selected from SEQ ID NOs: 5, 26, and 28.

39. The method according to claim 1, wherein said reverse primer comprises the nucleic acid sequence of SEQ ID NO: 5, or at least 25 consecutive nucleotides of SEQ ID NO: 5.

40. The method according to claim 1, wherein said forward primer comprises a nucleic acid sequence having at least 90% sequence identity to a nucleic acid sequence selected from SEQ ID NOs: 4, 8, 10, and 31, and wherein said reverse primer comprises a nucleic acid sequence having 90% sequence identity to a nucleic acid sequence selected from SEQ ID NOs: 5, 26, and 28.

41. The method according to claim 1, wherein said forward primer comprises a nucleic acid sequence selected from SEQ ID NOs: 4, 8, 10, and 31, and wherein said reverse primer comprises a nucleic acid sequence selected from SEQ ID NOs: 5, 26, and 28.

42. The method according to claim 1, wherein said forward primer comprises a nucleic acid sequence selected from SEQ ID NOs: 4, 8, and 31, and wherein said reverse primer comprises the nucleic acid sequence of SEQ ID NO: 5.

43. The method according to claim 7, wherein said forward and reverse oligonucleotide primers are at least 20 nucleotides long.

44. The method according to claim 7, wherein said detecting step comprises:
(a) contacting said amplified nucleic acid sequence with a probe, wherein the probe binds to a target site within said amplified nucleic acid sequence, or the complement thereof; and
(b) detecting binding of said probe to said amplified nucleic acid sequence.

45. The method according to claim 44, wherein the probe binds to a target site located between nucleotide residues 55 and 100 of the nucleic acid strand complementary to SEQ ID NO: 1.

46. The method according to claim 44, wherein said probe is at least 15 nucleotides long and up to 50 nucleotides long.

47. The method according to claim 46, wherein the probe comprises the nucleic acid sequence of SEQ ID NO: 3, or a fragment thereof having at least 15 nucleotides.

48. The method according to claim 44, wherein said probe is at least 15 nucleotides long and up to 20 nucleotides long.

49. The method according to claim 45, wherein said probe binds to a target site located between nucleotide residues 60 and 90 of the nucleic acid strand complementary to SEQ ID NO: 1.

50. The method according to claim 45, wherein said probe binds to a target site located between nucleotide residues 65 and 85 of the nucleic acid strand complementary to SEQ ID NO: 1.

51. The method according to claim 44, wherein said probe comprises the nucleic acid sequence of SEQ ID NO: 3.

52. The method according to claim 7, wherein said fragment of SEQ ID NO: 1 is at least 100 consecutive nucleotides of SEQ ID NO: 1 or at least 200 consecutive nucleotides of SEQ ID NO: 1.

53. The method according to claim 7, wherein said fragment of SEQ ID NO: 1 is up to 275 consecutive nucleotides of SEQ ID NO: 1.

54. The method according to claim 43, wherein said forward primer and/or said reverse oligonucleotide primer is between 25-30 nucleotides long.

55. The method according to claim 43, wherein said forward primer and/or said reverse oligonucleotide primer is between 45-55 nucleotides long.

56. The method according to claim 7, wherein said forward primer binds to a target site located between nucleotide residues 1-18 of a nucleic acid strand complementary to SEQ ID NO: 1, and said reverse primer binds to a target site located between nucleotide residues 214-240 of SEQ ID NO: 1.

57. The method according to claim 7, wherein the forward primer target site is located between nucleotide residue 76 and nucleotide residue 125 of a nucleic acid strand complementary to SEQ ID NO: 48.

58. The method according to claim 57, wherein the forward primer target site is located between nucleotide residue 81 and nucleotide residue 120 of a nucleic acid strand complementary to SEQ ID NO: 48.

59. The method according to claim 57, wherein the forward primer target site is located between nucleotide residue 86 and nucleotide residue 120 of a nucleic acid strand complementary to SEQ ID NO: 48.

60. The method according to claim 7, wherein said forward primer binds to a target site that comprises nucleotide residues 101-118 of a nucleic acid strand complementary to SEQ ID NO: 48.

61. The method according to claim 7, wherein said forward primer binds to a target site located from nucleotide residue 90 to nucleotide residue 118 of a nucleic acid strand complementary to SEQ ID NO: 48.

62. The method according to claim 7, wherein the forward primer target site is located between nucleotide residue 41 and nucleotide residue 101 of a nucleic acid strand complementary to SEQ ID NO: 48.

63. The method according to claim 62, wherein the forward primer target site is located between nucleotide residue 46 and nucleotide residue 101 of a nucleic acid strand complementary to SEQ ID NO: 48.

64. The method according to claim 7, wherein said forward primer binds to a target site located from nucleotide residue 48 to nucleotide residue 100 of a nucleic acid strand complementary to SEQ ID NO: 48.

65. The method according to claim 7, wherein said forward primer comprises a nucleic acid sequence having at least 90% sequence identity to a nucleic acid sequence selected from SEQ ID NOs: 4, 8, 10, or 31.

66. The method according to claim 7, wherein said forward primer comprises a nucleic acid selected from SEQ ID NOs: 4, 8, 10, and 31.

67. The method according to claim 7, wherein said forward primer comprises a nucleic acid sequence selected from SEQ ID NOs: 4, 8, and 31, or at least 27 consecutive nucleotides of SEQ ID NOs: 4, 8, or 31.

68. The method according to claim 7, wherein said reverse primer binds to a target site located between nucleotide residue 197 and nucleotide residue 297 of SEQ ID NO: 48.

69. The method according to claim 7, wherein said reverse primer binds to a target site located between nucleotide residue 198 and nucleotide residue 247 of SEQ ID NO: 48.

70. The method according to claim 7, wherein said reverse primer binds to a target site located between nucleotide residue 248 and nucleotide residue 350 of SEQ ID NO: 48.

71. The method according to claim 7, wherein the reverse primer target site is located from nucleotide residue 298 to nucleotide residue 347 of SEQ ID NO: 48.

72. The method according to claim 7, wherein said reverse primer binds to a target site located between nucleotide residue 300 and nucleotide residue 350 of SEQ ID NO: 48.

73. The method according to claim 7, wherein the reverse primer target site is located between nucleotide residue 310 and nucleotide residue 345 of SEQ ID NO: 48.

74. The method according to claim 7, wherein the reverse primer target site is located from nucleotide residue 314 and nucleotide residue 340 of SEQ ID NO: 48.

75. The method according to claim 7, wherein said reverse primer comprises a nucleic acid sequence having at least 90% sequence identity to a nucleic acid sequence selected from SEQ ID NOs: 5, 26, and 28.

76. The method according to claim 7, wherein said reverse primer comprises a nucleic acid sequence selected from SEQ ID NOs: 5, 26, and 28.

77. The method according to claim 7, wherein said reverse primer comprises the nucleic acid sequence of SEQ ID NO: 5, or at least 25 consecutive nucleotides of SEQ ID NO: 5.

78. The method according to claim 7, wherein said forward primer comprises a nucleic acid sequence having at least 90% sequence identity to a nucleic acid sequence selected from SEQ ID NOs: 4, 8, 10, and 31, and wherein said reverse primer comprises a nucleic acid sequence having 90% sequence identity to a nucleic acid sequence selected from SEQ ID NOs: 5, 26, and 28.

79. The method according to claim 7, wherein said forward primer comprises a nucleic acid sequence selected from SEQ ID NOs: 4, 8, 10, and 31, and wherein said reverse primer comprises a nucleic acid sequence selected from SEQ ID NOs: 5, 26, and 28.

80. The method according to claim 7, wherein said forward primer comprises a nucleic acid sequence selected from SEQ ID NOs: 4, 8, and 31, and wherein said reverse primer comprises the nucleic acid sequence of SEQ ID NO: 5.

81. The method according to claim 8, wherein said forward and reverse oligonucleotide primers are at least 20 nucleotides long.

82. The method according to claim 8, wherein said detecting step comprises:
(a) contacting said amplified nucleic acid sequence with a probe, wherein the probe binds to a target site within said amplified nucleic acid sequence, or the complement thereof; and
(b) detecting binding of said probe to said amplified nucleic acid sequence.

83. The method according to claim 82, wherein the probe binds to a target site located between nucleotide residues 55 and 100 of the nucleic acid strand complementary to SEQ ID NO: 1.

84. The method according to claim 82, wherein said probe is at least 15 nucleotides long and up to 50 nucleotides long.

85. The method according to claim 84, wherein the probe comprises the nucleic acid sequence of SEQ ID NO: 3, or a fragment thereof having at least 15 nucleotides.

86. The method according to claim 82, wherein said probe is at least 15 nucleotides long and up to 20 nucleotides long.

87. The method according to claim 83, wherein said probe binds to a target site located between nucleotide residues 60 and 90 of the nucleic acid strand complementary to SEQ ID NO: 1.

88. The method according to claim 83, wherein said probe binds to a target site located between nucleotide residues 65 and 85 of the nucleic acid strand complementary to SEQ ID NO: 1.

89. The method according to claim 82, wherein said probe comprises the nucleic acid sequence of SEQ ID NO: 3.

90. The method according to claim 8, wherein said fragment of SEQ ID NO: 1 is at least 100 consecutive nucleotides of SEQ ID NO: 1 or at least 200 consecutive nucleotides of SEQ ID NO: 1.

91. The method according to claim 8, wherein said fragment of SEQ ID NO: 1 is up to 275 consecutive nucleotides of SEQ ID NO: 1.

92. The method according to claim 81, wherein said forward primer and/or said reverse oligonucleotide primer is between 25-30 nucleotides long.

93. The method according to claim 81, wherein said forward primer and/or said reverse oligonucleotide primer is between 45-55 nucleotides long.

94. The method according to claim 8, wherein said forward primer binds to a target site located between nucleotide residues 1-18 of a nucleic acid strand complementary to SEQ ID NO: 1, and said reverse primer binds to a target site located between nucleotide residues 214-240 of SEQ ID NO: 1.

95. The method according to claim 8, wherein the forward primer target site is located between nucleotide residue 76 and nucleotide residue 125 of a nucleic acid strand complementary to SEQ ID NO: 48.

96. The method according to claim 95, wherein the forward primer target site is located between nucleotide residue 81 and nucleotide residue 120 of a nucleic acid strand complementary to SEQ ID NO: 48.

97. The method according to claim 95, wherein the forward primer target site is located between nucleotide residue 86 and nucleotide residue 120 of a nucleic acid strand complementary to SEQ ID NO: 48.

98. The method according to claim 8, wherein said forward primer binds to a target site that comprises nucleotide residues 101-118 of a nucleic acid strand complementary to SEQ ID NO: 48.

99. The method according to claim 8, wherein said forward primer binds to a target site located from nucleotide residue 90 to nucleotide residue 118 of a nucleic acid strand complementary to SEQ ID NO: 48.

100. The method according to claim 8, wherein the forward primer target site is located between nucleotide residue 41 and nucleotide residue 101 of a nucleic acid strand complementary to SEQ ID NO: 48.

101. The method according to claim 100, wherein the forward primer target site is located between nucleotide residue 46 and nucleotide residue 101 of a nucleic acid strand complementary to SEQ ID NO: 48.

102. The method according to claim 8, wherein said forward primer binds to a target site located from nucleotide residue 48 to nucleotide residue 100 of a nucleic acid strand complementary to SEQ ID NO: 48.

103. The method according to claim 8, wherein said forward primer comprises a nucleic acid sequence having at least 90% sequence identity to a nucleic acid sequence selected from SEQ ID NOs: 4, 8, 10, or 31.

104. The method according to claim 8, wherein said forward primer comprises a nucleic acid selected from SEQ ID NOs: 4, 8, 10, and 31.

105. The method according to claim 8, wherein said forward primer comprises a nucleic acid sequence selected from SEQ ID NOs: 4, 8, and 31, or at least 27 consecutive nucleotides of SEQ ID NOs: 4, 8, or 31.

106. The method according to claim 8, wherein said reverse primer binds to a target site located between nucleotide residue 197 and nucleotide residue 297 of SEQ ID NO: 48.

107. The method according to claim 8, wherein said reverse primer binds to a target site located between nucleotide residue 198 and nucleotide residue 247 of SEQ ID NO: 48.

108. The method according to claim 8, wherein said reverse primer binds to a target site located between nucleotide residue 248 and nucleotide residue 350 of SEQ ID NO: 48.

109. The method according to claim 8, wherein the reverse primer target site is located from nucleotide residue 298 to nucleotide residue 347 of SEQ ID NO: 48.

110. The method according to claim 8, wherein said reverse primer binds to a target site located between nucleotide residue 300 and nucleotide residue 350 of SEQ ID NO: 48.

111. The method according to claim 8, wherein the reverse primer target site is located between nucleotide residue 310 and nucleotide residue 345 of SEQ ID NO: 48.

112. The method according to claim 8, wherein the reverse primer target site is located from nucleotide residue 314 and nucleotide residue 340 of SEQ ID NO: 48.

113. The method according to claim 8, wherein said reverse primer comprises a nucleic acid sequence having at least 90% sequence identity to a nucleic acid sequence selected from SEQ ID NOs: 5, 26, and 28.

114. The method according to claim 8, wherein said reverse primer comprises a nucleic acid sequence selected from SEQ ID NOs: 5, 26, and 28.

115. The method according to claim 8, wherein said reverse primer comprises the nucleic acid sequence of SEQ ID NO: 5, or at least 25 consecutive nucleotides of SEQ ID NO: 5.

116. The method according to claim 8, wherein said forward primer comprises a nucleic acid sequence having at least 90% sequence identity to a nucleic acid sequence selected from SEQ ID NOs: 4, 8, 10, and 31, and wherein said reverse primer comprises a nucleic acid sequence having 90% sequence identity to a nucleic acid sequence selected from SEQ ID NOs: 5, 26, and 28.

117. The method according to claim 8, wherein said forward primer comprises a nucleic acid sequence selected from SEQ ID NOs: 4, 8, 10, and 31, and wherein said reverse primer comprises a nucleic acid sequence selected from SEQ ID NOs: 5, 26, and 28.

118. The method according to claim 8, wherein said forward primer comprises a nucleic acid sequence selected from SEQ ID NOs: 4, 8, and 31, and wherein said reverse primer comprises the nucleic acid sequence of SEQ ID NO: 5.

119. The method according to claim 9, wherein said forward and reverse oligonucleotide primers are at least 20 nucleotides long.

120. The method according to claim 9, wherein said detecting step comprises:
(a) contacting said amplified nucleic acid sequence with a probe, wherein the probe binds to a target site within said amplified nucleic acid sequence, or the complement thereof; and
(b) detecting binding of said probe to said amplified nucleic acid sequence.

121. The method according to claim 120, wherein the probe binds to a target site located between nucleotide residues 55 and 100 of the nucleic acid strand complementary to SEQ ID NO: 1.

122. The method according to claim 120, wherein said probe is at least 15 nucleotides long and up to 50 nucleotides long.

123. The method according to claim 122, wherein the probe comprises the nucleic acid sequence of SEQ ID NO: 3, or a fragment thereof having at least 15 nucleotides.

124. The method according to claim 120, wherein said probe is at least 15 nucleotides long and up to 20 nucleotides long.

125. The method according to claim 121, wherein said probe binds to a target site located between nucleotide residues 60 and 90 of the nucleic acid strand complementary to SEQ ID NO: 1.

126. The method according to claim 121, wherein said probe binds to a target site located between nucleotide residues 65 and 85 of the nucleic acid strand complementary to SEQ ID NO: 1.

127. The method according to claim 120, wherein said probe comprises the nucleic acid sequence of SEQ ID NO: 3.

128. The method according to claim 9, wherein said fragment of SEQ ID NO: 1 is at least 100 consecutive nucleotides of SEQ ID NO: 1 or at least 200 consecutive nucleotides of SEQ ID NO: 1.

129. The method according to claim 9, wherein said fragment of SEQ ID NO: 1 is up to 275 consecutive nucleotides of SEQ ID NO: 1.

130. The method according to claim 119, wherein said forward primer and/or said reverse oligonucleotide primer is between 25-30 nucleotides long.

131. The method according to claim 119, wherein said forward primer and/or said reverse oligonucleotide primer is between 45-55 nucleotides long.

132. The method according to claim 9, wherein said forward primer binds to a target site located between nucleotide residues 1-18 of a nucleic acid strand complementary to SEQ ID NO: 1, and said reverse primer binds to a target site located between nucleotide residues 214-240 of SEQ ID NO: 1.

133. The method according to claim 9, wherein the forward primer target site is located between nucleotide residue 76 and nucleotide residue 125 of a nucleic acid strand complementary to SEQ ID NO: 48.

134. The method according to claim 133, wherein the forward primer target site is located between nucleotide residue 81 and nucleotide residue 120 of a nucleic acid strand complementary to SEQ ID NO: 48.

135. The method according to claim 133, wherein the forward primer target site is located between nucleotide residue 86 and nucleotide residue 120 of a nucleic acid strand complementary to SEQ ID NO: 48.

136. The method according to claim 9, wherein said forward primer binds to a target site that comprises nucleotide residues 101-118 of a nucleic acid strand complementary to SEQ ID NO: 48.

137. The method according to claim 9, wherein said forward primer binds to a target site located from nucleotide residue 90 to nucleotide residue 118 of a nucleic acid strand complementary to SEQ ID NO: 48.

138. The method according to claim 9, wherein the forward primer target site is located between nucleotide residue 41 and nucleotide residue 101 of a nucleic acid strand complementary to SEQ ID NO: 48.

139. The method according to claim 138, wherein the forward primer target site is located between nucleotide residue 46 and nucleotide residue 101 of a nucleic acid strand complementary to SEQ ID NO: 48.

140. The method according to claim 9, wherein said forward primer binds to a target site located from nucleotide residue 48 to nucleotide residue 100 of a nucleic acid strand complementary to SEQ ID NO: 48.

141. The method according to claim 9, wherein said forward primer comprises a nucleic acid sequence having at least 90% sequence identity to a nucleic acid sequence selected from SEQ ID NOs: 4, 8, 10, or 31.

142. The method according to claim 9, wherein said forward primer comprises a nucleic acid selected from SEQ ID NOs: 4, 8, 10, and 31.

143. The method according to claim 9, wherein said forward primer comprises a nucleic acid sequence selected from SEQ ID NOs: 4, 8, and 31, or at least 27 consecutive nucleotides of SEQ ID NOs: 4, 8, or 31.

144. The method according to claim 9, wherein said reverse primer binds to a target site located between nucleotide residue 197 and nucleotide residue 297 of SEQ ID NO: 48.

145. The method according to claim 9, wherein said reverse primer binds to a target site located between nucleotide residue 198 and nucleotide residue 247 of SEQ ID NO: 48.

146. The method according to claim 9, wherein said reverse primer binds to a target site located between nucleotide residue 248 and nucleotide residue 350 of SEQ ID NO: 48.

147. The method according to claim 9, wherein the reverse primer target site is located from nucleotide residue 298 to nucleotide residue 347 of SEQ ID NO: 48.

148. The method according to claim 9, wherein said reverse primer binds to a target site located between nucleotide residue 300 and nucleotide residue 350 of SEQ ID NO: 48.

149. The method according to claim 9, wherein the reverse primer target site is located between nucleotide residue 310 and nucleotide residue 345 of SEQ ID NO: 48.

150. The method according to claim 9, wherein the reverse primer target site is located from nucleotide residue 314 and nucleotide residue 340 of SEQ ID NO: 48.

151. The method according to claim 9, wherein said reverse primer comprises a nucleic acid sequence having at least 90% sequence identity to a nucleic acid sequence selected from SEQ ID NOs: 5, 26, and 28.

152. The method according to claim 9, wherein said reverse primer comprises a nucleic acid sequence selected from SEQ ID NOs: 5, 26, and 28.

153. The method according to claim 9, wherein said reverse primer comprises the nucleic acid sequence of SEQ ID NO: 5, or at least 25 consecutive nucleotides of SEQ ID NO: 5.

154. The method according to claim 9, wherein said forward primer comprises a nucleic acid sequence having at least 90% sequence identity to a nucleic acid sequence selected from SEQ ID NOs: 4, 8, 10, and 31, and wherein said reverse primer comprises a nucleic acid sequence having 90% sequence identity to a nucleic acid sequence selected from SEQ ID NOs: 5, 26, and 28.

155. The method according to claim 9, wherein said forward primer comprises a nucleic acid sequence selected from SEQ ID NOs: 4, 8, 10, and 31, and wherein said reverse primer comprises a nucleic acid sequence selected from SEQ ID NOs: 5, 26, and 28.

156. The method according to claim 9, wherein said forward primer comprises a nucleic acid sequence selected from SEQ ID NOs: 4, 8, and 31, and wherein said reverse primer comprises the nucleic acid sequence of SEQ ID NO: 5.

* * * * *